(12) United States Patent
Green et al.

(10) Patent No.: US 12,059,476 B2
(45) Date of Patent: Aug. 13, 2024

(54) BIODEGRADABLE BIOMIMETIC PARTICLES

(71) Applicant: The Johns Hopkins University, Baltimore, MD (US)

(72) Inventors: Jordan J. Green, Baltimore, MD (US); Jonathan Schneck, Blatimore, MD (US); Alyssa K. Galaro, Baltimore, MD (US); Randall A. Meyer, Baltimore, MD (US); John W. Hickey, Baltimore, MD (US); Kelly Rhodes, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 524 days.

(21) Appl. No.: 16/754,951

(22) PCT Filed: Oct. 10, 2018

(86) PCT No.: PCT/US2018/055207
§ 371 (c)(1),
(2) Date: Apr. 9, 2020

(87) PCT Pub. No.: WO2019/075056
PCT Pub. Date: Apr. 18, 2019

(65) Prior Publication Data
US 2020/0230257 A1     Jul. 23, 2020

Related U.S. Application Data

(60) Provisional application No. 62/570,249, filed on Oct. 10, 2017.

(51) Int. Cl.
| | | |
|---|---|---|
| *A61K 47/62* | (2017.01) | |
| *A61K 47/68* | (2017.01) | |
| *A61K 47/69* | (2017.01) | |
| *C07K 16/28* | (2006.01) | |

(52) U.S. Cl.
CPC .......... *A61K 47/6927* (2017.08); *A61K 47/62* (2017.08); *A61K 47/6849* (2017.08); *C07K 16/2818* (2013.01); *C07K 16/2827* (2013.01); *C07K 16/2878* (2013.01)

(58) Field of Classification Search
CPC ................ A61K 47/6927; A61K 47/62; A61K 47/6849; C07K 16/2827; C07K 16/2878
See application file for complete search history.

(56) References Cited

U.S. PATENT DOCUMENTS

| | | | |
|---|---|---|---|
| 5,475,096 A | 12/1995 | Gold et al. | |
| 5,831,012 A | 11/1998 | Nilsson et al. | |
| 6,004,746 A | 12/1999 | Brent et al. | |
| 6,015,884 A | 1/2000 | Schneck et al. | |
| 6,140,113 A | 10/2000 | Schneck et al. | |
| 6,268,411 B1 | 7/2001 | Schneck et al. | |
| 6,448,071 B1 | 9/2002 | Schneck et al. | |
| 6,458,354 B1 | 10/2002 | Schneck et al. | |
| 6,794,144 B1 | 9/2004 | Saksela et al. | |
| 6,818,418 B1 | 11/2004 | Lipovsek et al. | |
| 6,994,982 B1 | 2/2006 | Watt et al. | |
| 7,166,697 B1 | 1/2007 | Galanis et al. | |
| 7,186,524 B2 | 3/2007 | Kolmar et al. | |
| 7,250,297 B1 | 7/2007 | Beste et al. | |
| 7,417,130 B2 | 8/2008 | Stumpp et al. | |
| 7,427,394 B2* | 9/2008 | Anderson | C12N 15/88 424/78.37 |
| 7,803,907 B2 | 9/2010 | Stemmer et al. | |
| 7,838,629 B2 | 11/2010 | Fiedler et al. | |
| 8,287,849 B2 | 10/2012 | Langer et al. | |
| 2004/0023334 A1 | 2/2004 | Prior | |
| 2004/0132094 A1 | 7/2004 | Etzerodt et al. | |
| 2004/0146938 A1 | 7/2004 | Nguyen et al. | |
| 2004/0157209 A1 | 8/2004 | Yilmaz et al. | |
| 2004/0209249 A1 | 10/2004 | Nixon et al. | |
| 2010/0119446 A1 | 5/2010 | Grabulovski et al. | |
| 2010/0239633 A1 | 9/2010 | Strome et al. | |

(Continued)

FOREIGN PATENT DOCUMENTS

| | | |
|---|---|---|
| WO | WO 2014/066811 | 5/2014 |
| WO | WO 2014/066898 | 5/2014 |

(Continued)

OTHER PUBLICATIONS

Makadia. Poly Lactic-co-Glycolic Acid (PLGA) as Biodegradable Controlled Drug Delivery Carrier, Polymers (Basel). Sep. 1, 2011; 3(3): 1377-1397. (Year: 2011).*

Sunshine, et al. "Effects of Base Polymer Hydrophobicity and End-Group Modification on Polymeric Gene Delivery," Biomacromolecules 2011, 12, 3592-3600. (Year: 2011).*

Hermanson, Bioconjugate Techniques, Academic Press, New York, 1996. TOC only. 2 pages.

(Continued)

*Primary Examiner* — Michael P Cohen
(74) *Attorney, Agent, or Firm* — Casimir Jones, SC; Jeffrey W. Childers

(57) ABSTRACT

The present invention provides biodegradable, biomimetic particles for interacting with cells, including immune cells. In various embodiments, the particles comprise a polymer blend comprising a polyester, such as poly(lactic-co-glycolic acid) (PLGA) and a polyamine, such as poly(beta-amino ester) (PBAE). The particles further comprise, on their surface, one or more ligands for one or more cell surface receptor(s) or cell surface molecule(s). In some embodiments, the cell surface receptor or cell surface molecule is on an immune cell, such as a lymphocyte (T cell or B cell), natural killer cell, dendritic cell, or other cell of the immune system or tumor microenvironment.

34 Claims, 16 Drawing Sheets

(56) References Cited

U.S. PATENT DOCUMENTS

| | | | |
|---|---|---|---|
| 2012/0114759 A1 | 5/2012 | Green et al. | |
| 2012/0128782 A1 | 5/2012 | Green et al. | |
| 2014/0037736 A1 | 2/2014 | Shi et al. | |
| 2014/0370099 A1* | 12/2014 | Green | A61K 39/0001 424/234.1 |
| 2015/0366991 A1 | 12/2015 | Schneck et al. | |
| 2016/0122390 A1 | 5/2016 | Popel et al. | |
| 2016/0251477 A1* | 9/2016 | Cui | C12N 15/111 424/490 |
| 2017/0119668 A1 | 5/2017 | Keselowsky et al. | |
| 2017/0246277 A1 | 8/2017 | Schneck et al. | |

FOREIGN PATENT DOCUMENTS

| | | | | |
|---|---|---|---|---|
| WO | WO-2014066811 A1 * | 5/2014 | | A61K 31/713 |
| WO | WO 2017/172769 | 10/2017 | | |

OTHER PUBLICATIONS

Meyer et al., An automated multidimensional thin film stretching device for the generation of anisotropic polymeric micro- and nanoparticles. JBMR Part A, 2015, 103(8), 2747-2757. 30 pages.

Storz. Intellectual property protection: strategies for antibody inventions. MAbs. May-Jun. 2011;3(3):310-7.

Tan et al., Induction of alloantigen-specific hyporesponsiveness in human T lymphocytes by blocking interaction of CD28 with its natural ligand B7/BB1. J Exp Med. Jan. 1, 1993;177(1):165-73.

Vitale et al., Effect of tumor cells and tumor microenvironment on NK-cell function. Eur J Immunol. Jun. 2014;44(6):1582-92.

International Search Report and Written Opinion for PCT/US18/55207. Mailed Dec. 17, 2018. 7 pages.

Neshat et al., Improvement of Islet Engrafts via Treg Induction Using Immunomodulating Polymeric Tolerogenic Microparticles. ACS Biomater Sci Eng. Jun. 12, 2023;9(6):3522-3534.

Rhodes et al., Biodegradable Cationic Polymer Blends for Fabrication of Enhanced Artificial Antigen Presenting Cells to Treat Melanoma. ACS Appl Mater Interfaces. Feb. 24, 2021;13(7):7913-7923.

Rhodes et al., Bioengineered particles expand myelin-specific regulatory T cells and reverse autoreactivity in a mouse model of multiple sclerosis. Sci Adv. Jun. 2, 2023;9(22):eadd8693. 14 pages.

Rhodes et al., Biomimetic tolerogenic artificial antigen presenting cells for regulatory T cell induction. Acta Biomater. Aug. 2020:112:136-148.

* cited by examiner

PLGA  PLGA/PBAE

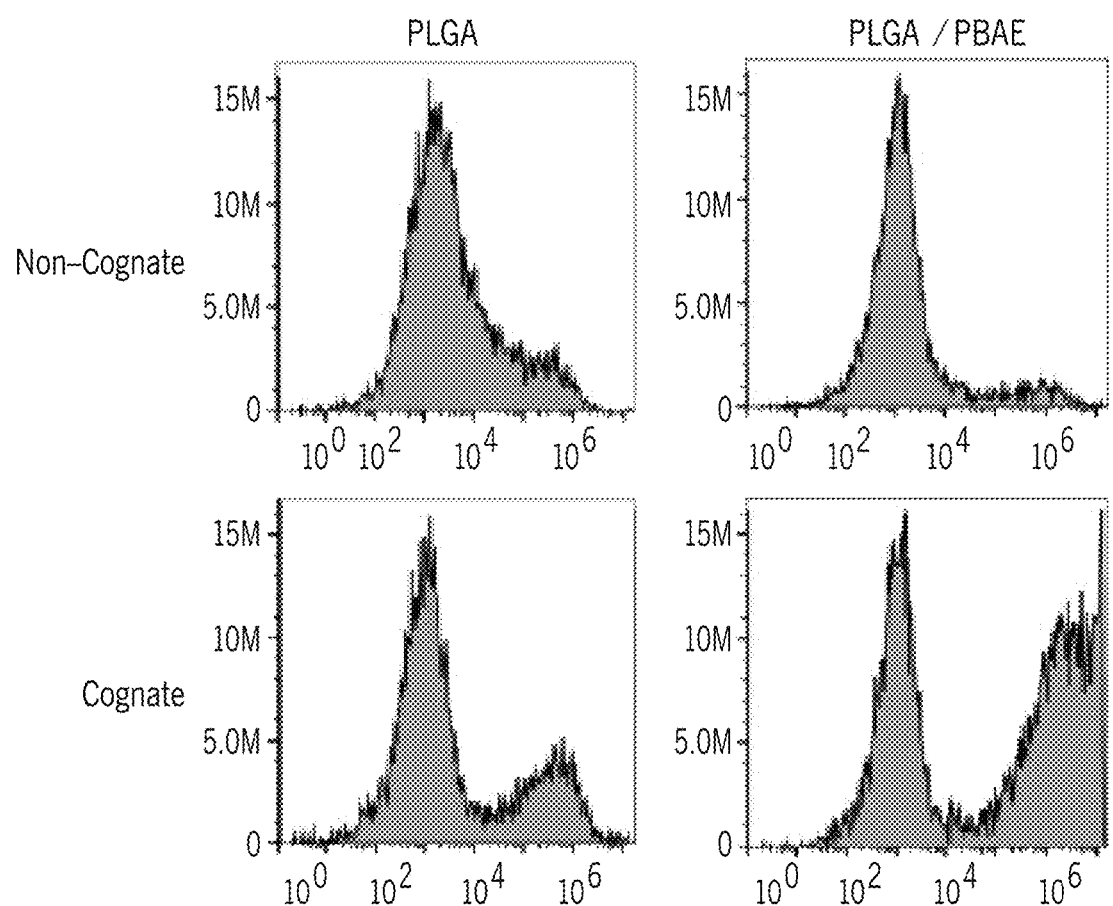

Particle Dose

BIODEGRADABLE BIOMIMETIC PARTICLES

PRIORITY

This application claims the benefit of U.S. Provisional Patent Application No. 62/570,249, filed on Oct. 10, 2017, which is incorporated herein by reference in its entirety.

STATEMENT OF RIGHTS TO INVENTIONS MADE UNDER FEDERALLY SPONSORED RESEARCH

This invention was made with government support under EB016721, awarded by the National Institutes of Health. The government has certain rights in the invention.

BACKGROUND

Particle platforms presenting immune cell ligands have promise for modulating immune cell activity both ex vivo and in vivo. For example, artificial antigen presenting cells (aAPCs) are a promising platform for activating and expanding antigen-specific T cells ex vivo or in vivo. aAPCs can present a "signal 1", a peptide antigen in the context of MHC class I or II molecular complex, and a "signal 2", a T cell costimulatory ligand, to activate and expand antigen-specific T cells. However, particle platforms used to date, such as PLGA, do not provide ideal levels of activity, which limits their practical utility.

In various aspects and embodiments, the present invention addresses these needs.

SUMMARY

The present invention provides biodegradable, biomimetic particles for interacting with cells, including immune cells and/or cells of the tumor microenvironment, as well as methods of use. In various embodiments, the particle comprises a polymer blend of at least one polyester and at least one polyamine, and comprises on its surface, one or more ligands for one or more cell surface receptor(s) or cell surface molecule(s). Exemplary polyesters comprise one or more of poly(lactic-co-glycolic acid) (PLGA), polycaprolactone (PCL), polyglycolic acid (PGA), polylactic acid (PLA), and polyhydroxyalkanoate (PHA), among others. Exemplary polyamines include polymers having one or more secondary or tertiary amines in a repeating backbone structure, such as a poly(beta-amino ester) (PBAE), including the polymers structures disclosed herein, or in some embodiments polyethylenimine (PEI). In some embodiments, the polymer blend comprises poly(lactic-co-glycolic acid) (PLGA) and poly(beta-amino ester) (PBAE).

In some embodiments, the ligand(s) interact and/or crosslink and/or cluster cell surface receptors or cell surface molecules on an immune cell, such as a lymphocyte (T cell or B cell), natural killer cell, dendritic cell, or other cell of the immune system, or a cell surface receptor or ligand present in the tumor microenvironment. The particles disclosed herein have desirable properties for driving immune cell function, including in some embodiments the potential to present a greater density of ligand (e.g., as compared to PLGA particles) as well as the ability to better mimic the physical dynamics of a cell-to-cell interface.

In various embodiments, the particle is a microparticle having an average diameter of from about 1 micron to about 5 microns. Microparticles can have the advantage of approximating the size of the cell or may mimic the cell-cell interface, which can be desirable particularly in embodiments where crosslinking or clustering of cell surface receptors is desirable (such as with aAPCs for expansion of lymphocytes).

In some embodiments, the particle is a nanoparticle having an average diameter of from about 50 nm to about 1 micron. Nanoparticles are often desirable for in vivo applications. For example, nanoscale particles (e.g., less than about 500 nm or less than 200 nm) will better distribute to target tissues such as lymph nodes, spleen, and tumor sites. In some embodiments, the particle has an average diameter of from about 50 nm to about 300 nm, or from 50 to 150 nm.

The particle comprises a ratio of polyester (e.g., PLGA) to polyamine polymers (e.g., PBAE) that is from about 10:1 to about 1:10. In some embodiments, the ratio of polyester to polyamine is from about 10:1 to about 1:1, or from about 8:1 to about 2:1, or from about 6:1 to about 3:1. For example, the ratio of polyester to polyamine is about 2:1, about 3:1, about 4:1, about 5:1, about 6:1, or about 7:1. In various embodiments, the particle comprises from about 10% to about 50% polyamine (e.g., PBAE), or from about 10% to about 40% polyamine (e.g., PBAE). In some embodiments, the PBAE has the structure of Structure 1, Structure 2, or Structure 3, as described herein. The particles may include blends of other polymer materials to modulate the surface properties.

Ligands and molecular complexes described herein can be chemically conjugated to the particles using any available process, including in a site directed manner to control orientation on the particles. In embodiments, ligands and protein complexes are conjugated, e.g., functionalized, to the particles using EDC/NHS (1-ethyl-3-(3-dimethylaminopropyl)carbodiimide hydrochloride/N hydroxysuccinimide) chemistry.

In various embodiments, the particles support higher levels (e.g., higher density) of ligand conjugation (as compared to PLGA particles, for example), which can provide for certain advantages in lymphocyte activation when particles are used for aAPC platforms, or for NK cell activation. In still other embodiments, ligands are non-specifically coupled to the particles, without linkers that provide activation chemistry.

In some embodiments, at least one ligand is a monoclonal antibody or fragment or portion thereof, the monoclonal antibody or fragment or portion thereof having binding specificity for a receptor or other target on the surface of an immune cell.

In some embodiments, the particle is an artificial antigen presenting cell (aAPC). These aAPCs in various embodiments can stimulate and activate immune cells in vitro at 100× lower doses than PLGA-only aAPCs; and can stimulate an endogenous response in vivo, an effect that has proven elusive with biodegradable aAPCs. aAPCs generally comprise one or more ligands that are an antigen presenting complex. Antigen presenting complexes may comprise an antigen binding cleft, which harbors an antigen for presentation to a T cell or T cell precursor. Antigen presenting complexes can be, for example, MHC class I or class II molecules.

A variety of antigens can be bound to antigen presenting complexes. The nature of the antigens depends on the type of antigen presenting complex that is used. For example, peptide antigens can be bound to MHC class I and class II peptide binding clefts. Non-classical MHC-like molecules can be used to present non-peptide antigens such as phospholipids, complex carbohydrates, and the like (e.g., bacterial membrane components such as mycolic acid and lipoarabinomannan). Any peptide capable of inducing an immune response can be bound to an antigen presenting complex. Antigenic peptides include tumor-associated antigens, autoantigens, alloantigens, and antigens of infectious agents.

In various embodiments, the particle (including and not limited to embodiments in which the particle is an aAPC) comprises a lymphocyte stimulatory or co-stimulatory molecule ("signal 2"). The stimulatory molecule may be a molecule that has a biological effect on a precursor T cell, a naive T cell, or on an antigen-specific T cell. Such molecules include, but are not limited to, molecules that specifically bind to CD28 (including antibodies), CD80 (B7-1), CD86 (B7-2), B7-H3, 4-1BB, 4-1BBL, CD27, CD30, CD 134 (OX-40L), B7h (B7RP-1), CD40, LIGHT, antibodies that specifically bind to HVEM, antibodies that specifically bind to CD40L, antibodies that specifically bind to OX40, and antibodies that specifically bind to 4-1BB.

In some embodiments, the particle comprises one or more ligands to redirect T cells (e.g., antigen-specific T cells) to tumors or cancer cells by presenting a ligand for a tumor or cancer cell surface marker. An exemplary marker is CD19, which can be targeted with anti-CD19 monoclonal antibodies. CD19 is useful for targeting B cell lymphomas, for example. In some embodiments, the cell surface molecule is her2, which can be targeted on breast cancer cells with anti-her2 monoclonal antibodies, for example.

In some embodiments, the particles comprise one or more ligands that are lymphocyte activating molecules together with an immune checkpoint blocking molecule. Such particles are termed "immunoswitch" particles. Exemplary immune checkpoint blocking molecules include PD-1 (e.g., to sequester PD-1L signals), anti-PD-1, or anti-PD-1L. In some embodiments, the immune checkpoint blocking molecule is anti-CTLA4. In some embodiments, one or more stimulatory ligands are selected from an agonist for CD28, a 4-1BB agonist such as 4-1BBL or an antibody against 4-1BB, an OX-40 agonist such as OX-40 or an antibody against OX-40, and an ICOS agonist such as ICOS-L or antibody against ICOS.

In some embodiments, the particle comprises an OX-40 agonist such as anti-CD134 (OX40), a 4-1BB agonist such as anti-CD137 (4-1BB), or a both an OX-40 agonist and a 4-1BB agonist, such as anti-CD134 and anti-CD137. Particles in these embodiments are potent activators of NK cells.

In other aspects, the invention provides pharmaceutical compositions comprising the particles as described herein and a pharmaceutically-acceptable excipient. The compositions can be formulated for administered to patients by any appropriate route. In some embodiments, the composition is lyophilized, and reconstituted prior to administration to a patient.

The particles and pharmaceutical compositions described herein are useful for immunotherapy, for example, in methods for activating immune cells or inducing the formation of antigen-specific cytotoxic T cells, either ex vivo or by administering an effective amount of the composition to a patient in need. The invention provides particle-based platforms for activating immune cells, such as, without limitation, T cells (including antigen-specific CTLs or helper T cells), B cells, natural killer cells, or dendritic cells, and/or for targeting the immunosuppressive nature of the tumor microenvironment.

In various embodiments, the invention provides methods for treating a disease or disorder, including but not limited to cancer, in a subject comprising administering to the subject the particles or compositions described herein. In some embodiments, the cancer is a hematological malignancy, carcinoma, or sarcoma. In other embodiments, the disease is an infectious disease, such as a viral or fungal infection, or is an autoimmune disease requiring activation or proliferation of regulatory T cells.

Embodiments of the invention will now be described with reference to the Drawings and following Detailed Description.

BRIEF DESCRIPTION OF THE DRAWINGS

FIG. 3C includes flow cytometry histograms showing higher binding of PLBA/PBAE aAPCs to cognate cells than binding of PLGA aAPCs to cognate cells.

Immunoswitch particles combine agonistic anti-4-1BB monoclonal antibodies and antagonistic anti-PD-L1 monoclonal antibodies on the surface of nanoparticles. The efficacy of iron-dextran-based immunoswitch particles has been demonstrated in their ability to induce CD8+ T cell activation when co-incubated with cognate tumor cells. To study the ability of PLGA/PBAE to serve as a platform for immunoswitch particles, immunoswitch particles were constructed from PLGA/PBAE nanoparticles and co-incubated with 2C CD8+ T cells and cognate B16-SIY tumor cells. PLGA/PBAE particles were added to culture at doses ranging from 0.001-1 mg particles/ml. IFN-γ release was measured.

Figure 7:
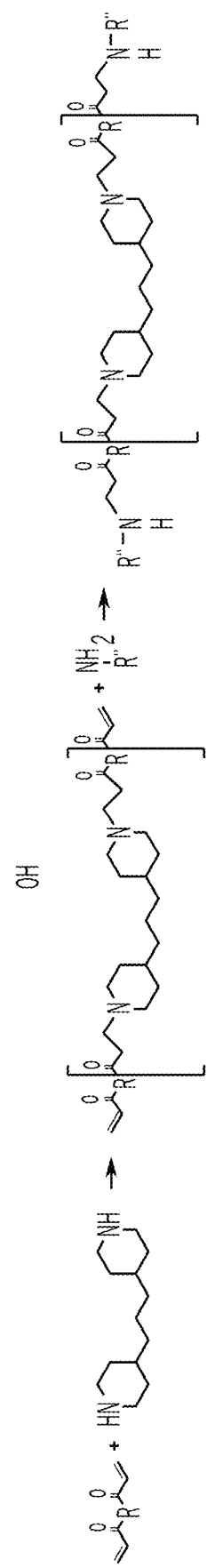

FIG. 7 shows a scheme for synthesis of PBAE according to Structure II.

Figure 8:
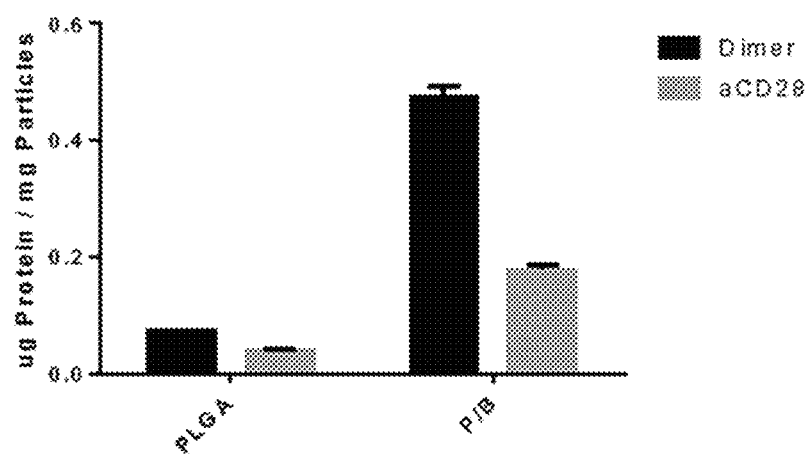

FIG. 8 is a graph showing that PLGA/PBAE aAPC microparticles (P/B) lead to a greater amount of protein on their surfaces, such as Signal 1 Dimer and Signal 2 aCD28, than PLGA aAPC microparticles when fabricated under the same conditions.

Figure 9:
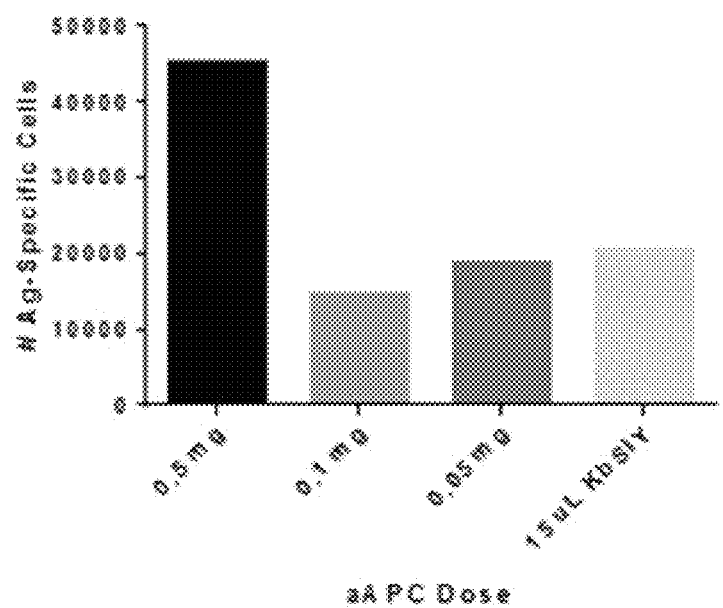

FIG. 9 is a graph showing that PLGA/PBAE aAPC microparticles expand the endogenous repertoire of T cells ex vivo.

Figure 10:
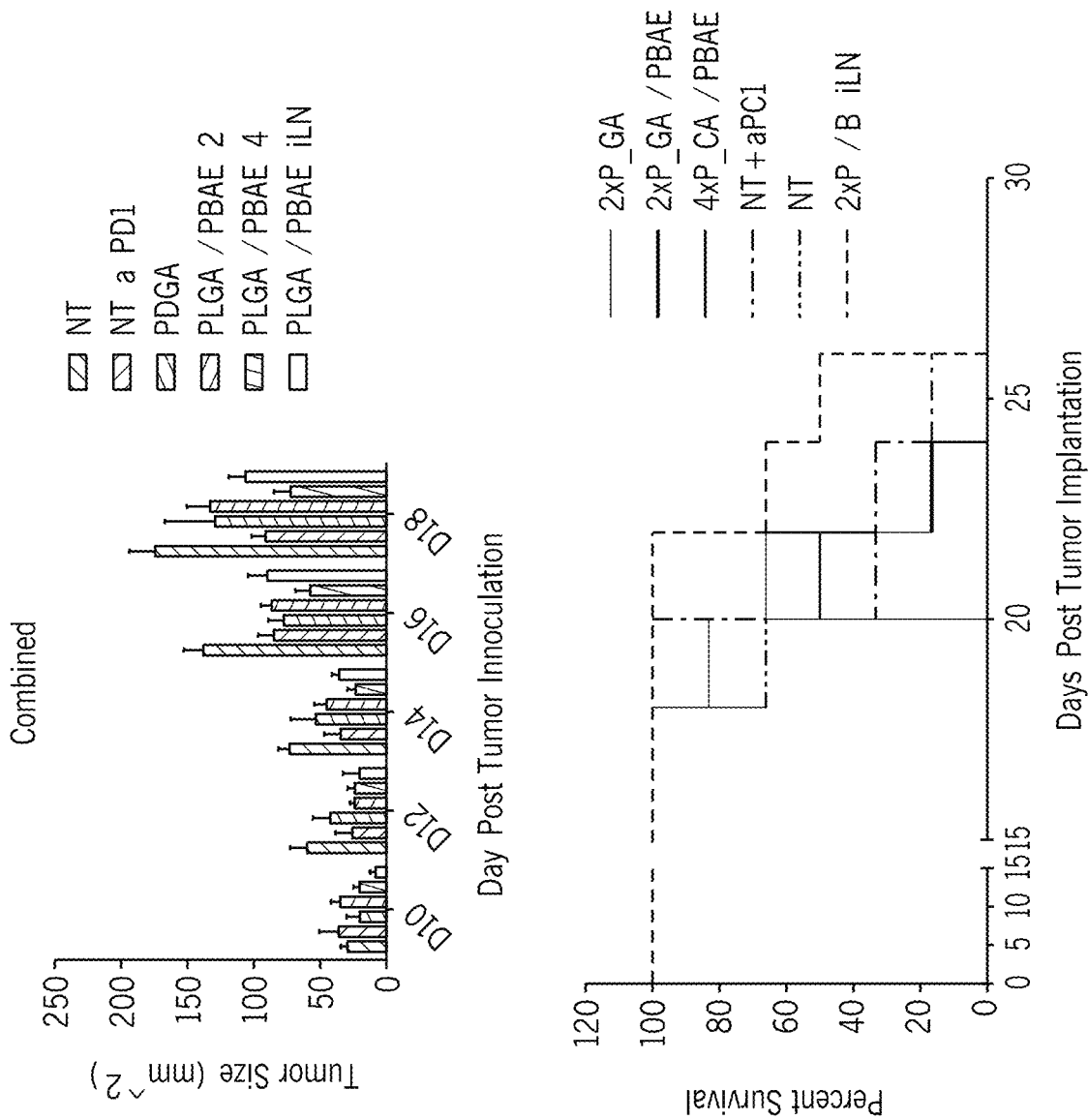

FIG. 10 are graphs showing that PLGA/PBAE aAPC particles can be administered either intravenously (blue/green) or intra-lymph node (purple) to stimulate endogenous cytotoxic T cells to attack and decrease the growth of a melanoma tumor in a mouse model.

DETAILED DESCRIPTION

The present invention provides biodegradable, biomimetic particles for interacting with cells, including immune cells, as well as methods of use. In various embodiments, the particle comprises a polymer blend of a polyester and a polyamine (which may also be a polyester), and comprises on its surface, one or more ligands for one or more cell surface receptor(s) or cell surface molecule(s).

Exemplary polyesters comprise one or more of poly (lactic-co-glycolic acid) (PLGA), polycaprolactone (PCL), polyglycolic acid (PGA), polylactic acid (PLA), and polyhydroxyalkanoate (PHA), among others. Exemplary polyamines include a poly(beta-amino ester) (PBAE), including polymers structures disclosed herein, or in some embodiments polyethylenimine (PEI). In some embodiments, the polymer blend comprises poly(lactic-co-glycolic acid) (PLGA) and poly(beta-amino ester) (PBAE). In various embodiments, the particles comprise a polymer blend of poly(lactic-co-glycolic acid) (PLGA) with a poly(beta-amino ester) (PBAE).

The particles further comprise, on their surface, one or more ligands for one or more cell surface receptor(s) or cell surface molecule(s). In some embodiments, the cell surface receptor or cell surface molecule is on an immune cell, such as a lymphocyte (T cell or B cell), natural killer cell, dendritic cell, or other cell of the immune system. The particles disclosed herein have desirable properties for driving immune cell function, including in some embodiments the potential to present a greater density of ligand on the surface (e.g., as compared to PLGA particles) as well as the ability to better mimic a cell-to-cell interface. For example, without being bound by theory, the elastic modulus of the particle may be more suitable for functional interaction with immune cells.

In some embodiments, the polyester comprises PLGA, which can be tuned for a specific biodegradation rate in vivo (by adjusting the LA:GA ratio and/or molecular weight of the PLGA polymer). In embodiments, the PLGA is based on a LA:GA ratio of from 20:1 to 1:20, including compositions of L/G of: 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. PLGA degrades by hydrolysis of its ester linkages. The time required for degradation of PLGA is related to the ratio of monomers: the higher the content of glycolide units, the lower the time required for degradation as compared to predominantly lactide units. In some embodiments, the PLGA is 50/50. In some embodiments, the particles comprise PLA and/or PGA instead of or in addition to PLGA.

In some embodiments, the polyamine further comprises biodegradable ester linkages. For example, the polyamine may comprise poly(beta-amino ester) (PBAE), which are biodegradable and biocompatible polymers. The polymers have tertiary amines in the backbone of the polymer, for example, the polymers may have about one or two tertiary amines per repeating backbone unit. The secondary or tertiary amines may comprise bivalent amine-containing heterocyclic groups, such as a piperidinyl. The polymers may also be co-polymers in which one of the components is a poly(beta-amino ester). The polymers of the invention may readily be prepared by condensing bis(secondary amines) or primary amines with bis(acrylate esters).

As used herein, "biodegradable" particles and/or polymer formulations are those that, when introduced into a subject, are broken down by the cellular machinery, by extracellular machinery, or by hydrolysis into components. The components preferably do not induce inflammation or other adverse effects in vivo. In embodiments, the chemical reactions relied upon to break down the biodegradable compositions are uncatalyzed (e.g., non-enzymatic).

Exemplary PBAE polymers are disclosed in U.S. Pat. No. 8,287,849, WO/2012/0128782, WO/2012/0114759, WO/2014/066811, WO/2014/066898, and US2016/0122390, each of which is incorporated herein by reference in its entirety.

In some embodiments, the PBAE is a polymer of the general Structure I or Structure II, where n is an integer of from 1 to 10,000. For example, n can be an integer of from 1 to 1000, or from 5 to 500, or from 5 to 200, or from 5 to 100, or from 5 to 20, or from 10 to 100, or from 10 to 50.

Structure I

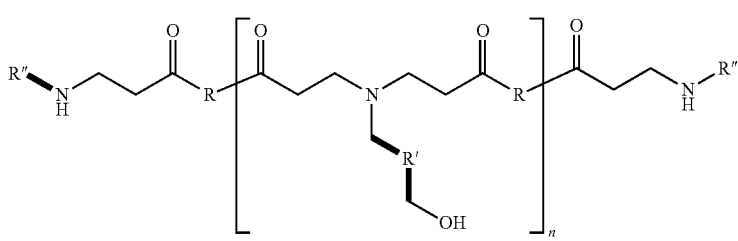

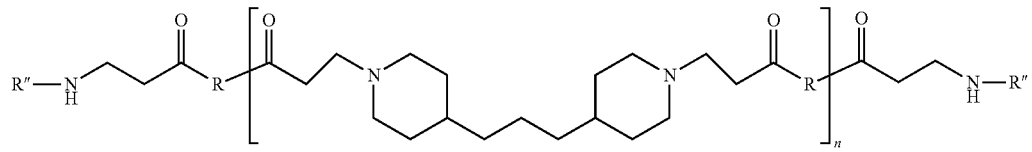

Structure II

For example, in some embodiments, the PBAE backbone is synthesized with a bivalent piperidine-containing group, which may include two piperidine groups linked by a C2 to C6 alkylene, such as the following group:

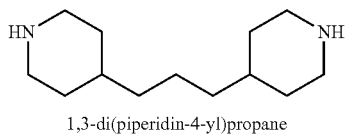 [SMILES: C(CC1CCNCC1)CC1CCNCC1]

1,3-di(piperidin-4-yl)propane

In some embodiments, R″ is an end group ("E") comprising an amine-containing heterocycle, which may include one or two secondary or tertiary amines. In some embodiments, R″ is an end group having the structure E7:

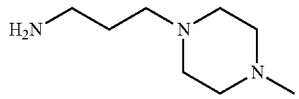

1,(3-aminopropyl)-4-methylpiperazine

In general Structures I or II, R comprises a backbone of a diacrylate, which may be selected from one or more of:

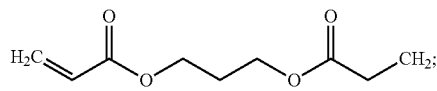

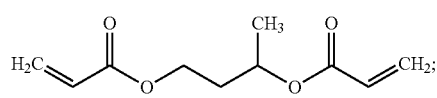

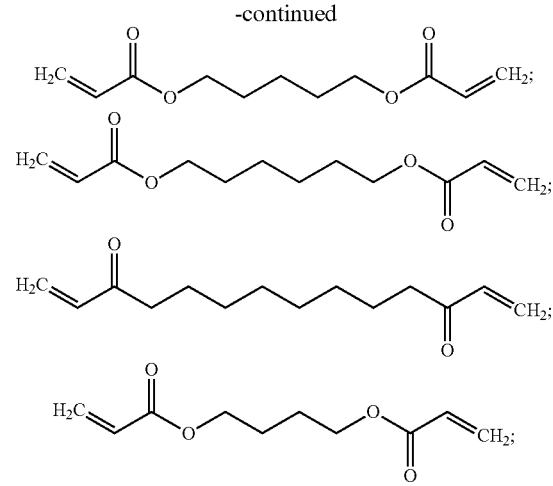

Thus, R is some embodiments forms (together with the groups to which it is attached) a linear or branched C3 to C7 diester.

In Structure I, R' generally comprises any side chain, and may be a C1 to C8 linear or branched alkylene, which is optionally substituted. Exemplary substituents include hydroxyl, alkyl, alkenyl, thiol, amine, carbonyl, and halogen.

R″ comprises is an end group, which may include one or more primary, secondary or tertiary amines, and may include aromatic and non-aromatic carbocyclic and heterocyclic groups, such as carbocyclic and heterocyclic groups of 5 or 6 atoms. R″ may comprise one or more ether, thioether, or disulfide linkages.

In some embodiments, the PBAE is of the following structure (Structure III):

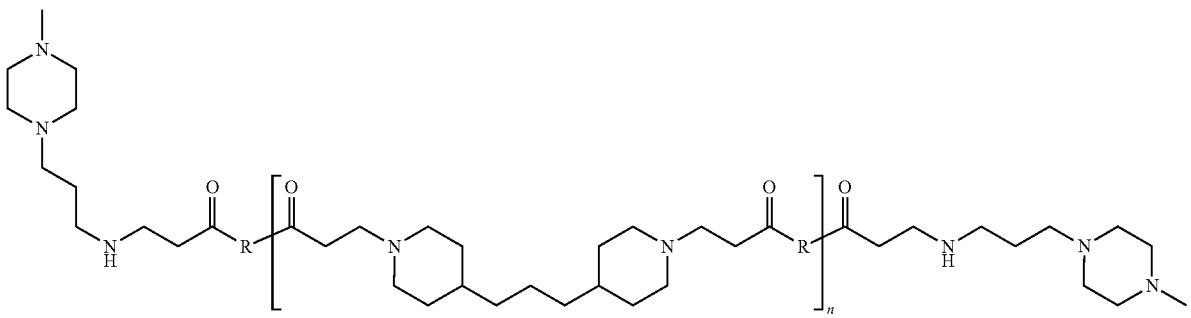

In some embodiments, the PBAE polymer has a molecular weight of from 5 to 10 kDa, or a molecular weight of from 10 to 15 kDa, or a molecular weight of from 15 to 25 kDa, or a molecular weight of from 25 to 50 kDa.

In embodiments, particles may comprise other combinations of cationic polymeric blends or block co-polymers. Additional polymers include polycaprolactone (PCL), polyglycolic acid (PGA), polylactic acid (PLA), poly (acrylic acid) (PAA), poly-3-hydroxybutyrate (P3HB), poly (hydroxybutyrate-co-hydroxyvalerate), and polyethylene glycol (PEG). In some embodiments, PEG is used as a block co-polymer with PLGA and/or PBAE.

In various embodiments, the particle is a microparticle having an average diameter of from about 1 micron to about 5 microns. Microparticles can have the advantage of approximating the size of the cell or may mimic the cell-cell interface, which can be desirable particularly in embodiments where crosslinking or clustering of cell surface receptors is desirable (such as with aAPCs for expansion of lymphocytes). In some embodiments, the particle has an average diameter of from about 1 to about 3 microns.

In some embodiments, the particle is a nanoparticle having an average diameter of from about 50 nm to about 1 micron. Nanoparticles are usually desirable for in vivo applications. For example, nanoscale aAPCs (e.g., less than about 500 nm) will better distribute to target tissues such as lymph nodes, spleen, and tumor sites. In some embodiments, the particle has an average diameter of from about 50 nm to about 500 nm, of from about 50 nm to about 300 nm, or from about 50 nm to about 200 nm, or from about 50 nm to about 150 nm. In some embodiments, the nanoparticle has an average diameter of from about 200 nm to about 500 nm.

The particle comprises a ratio of polyester (e.g., PLGA) to polyamine (e.g., PBAE) of from about 10:1 to about 1:10. The ratio of the polymers can tune the elastic modulus of the particles, which in some embodiments has a positive impact on the potential to drive immune cell activation. In some embodiments, the ratio of polyester (e.g., PLGA) to polyamine (e.g., PBAE) is from about 10:1 to about 1:1, or from about 8:1 to about 2:1, or from about 6:1 to about 3:1. For example, the ratio of polyester (e.g., PLGA) to polyamine (e.g., PBAE) is about 2:1, about 3:1, about 4:1, about 5:1, about 6:1, or about 7:1. In various embodiments, the particle comprises from about 10% to about 50% PBAE, or from about 10% to about 40% PBAE.

Ligands and molecular complexes described herein can be chemically conjugated to the particles using any available process. Functional groups for ligand binding include COOH, $NH_2$, SH, maleimide, pyridyl disulfide and acrylate. See, e.g., Hermanson, BIOCONJUGATE TECHNIQUES, Academic Press, New York, 1996. Activating functional groups include alkyl and acyl halides, amines, sulfhydryls, aldehydes, unsaturated bonds, hydrazides, isocyanates, isothiocyanates, ketones, azide, alkyne-derivatives, anhydrides, epoxides, carbonates, aminoxy, furan-derivatives and other groups known to activate for chemical bonding. In some embodiments, a molecule can be bound to the particle through the use of a small molecule-coupling reagent. Non-limiting examples of coupling reagents include carbodiimides, maleimides, N-hydroxysuccinimide esters, bischloroethylamines, and functional aldehydes such as glutaraldehyde, anhydrides and the like. In other embodiments, a molecule can be coupled to the particle through affinity binding such as a biotin-streptavidin linkage or coupling, as is well known in the art. For example, streptavidin can be bound to a solid support by covalent or non-covalent attachment, and a biotinylated molecule can be synthesized using methods that are well known in the art.

In some embodiments, ligands are conjugated to the beads through the use of cross-linkers containing n-hydro-succinimido (NHS) esters which react with amines on proteins. Alternatively, the cross-linkers are employed that contain active halogens that react with amine-, sulfhydryl-, or histidine-containing proteins, or cross-linkers containing epoxides that react with amines or sulfhydryl groups, or between maleimide groups and sulfhydryl groups. In embodiments, ligands and protein complexes are conjugated, e.g., functionalized, to the particles using EDC/NHS (1-ethyl-3-(3-dimethylaminopropyl)carbodiimide hydrochloride/N hydroxysuccinimide) chemistry, which conjugates carboxyl groups of protein ligands to PLGA. In some embodiments, ligands can be engineered with site-specific functional groups (example, such as a free cysteine), to provide consistent, site-directed, attachment to particles. Site directed attachment can be to functional groups of the selected polymers, including amines. In these embodiments, functional domains of ligands can be directed toward the environment and away from the particle surface. These embodiments further provide a controlled orientation more suitable for off-the-shelf pharmaceutical products.

In various embodiments, the particles support higher levels (e.g., higher density) of ligand conjugation (as compared to PLGA particles, for example), which can provide for certain advantages in lymphocyte activation when particles are used for aAPC platforms, or for NK cell activation. In still other embodiments, ligands are non-specifically coupled to the particles, without linkers or activation chemistry.

In some embodiments, at least one ligand is a monoclonal antibody or fragment or portion thereof, the monoclonal antibody or fragment or portion thereof having binding specificity for a receptor or other target on the surface of an immune cell.

As used herein, the term "antibody" includes antibodies and antigen-binding portions thereof. In some embodiments, the ligand is an antibody or antibody mimetic, such as a single-domain antibody, a recombinant heavy-chain-only antibody (VHH), a single-chain antibody (scFv), a shark heavy-chain-only antibody (VNAR), a microprotein (cysteine knot protein, knottin), a DARPin, a Tetranectin, an Affibody; a Transbody, an Anticalin, an AdNectin, an Affilin, a Microbody, a peptide aptamer, a phylomer, a stradobody, a maxibody, an evibody, a fynomer, an armadillo repeat protein, a Kunitz domain, an avimer, an atrimer, a probody, an immunobody, a triomab, a troybody, a pepbody, a vaccibody, a UniBody, a DuoBody, a Fv, a Fab, a Fab', a F(ab')2, a peptide mimetic molecule, or a synthetic molecule, or as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the particle is an artificial antigen presenting cell (aAPC). These aAPCs in various embodiments can stimulate and activate immune cells in vitro at 100× lower doses than PLGA-only aAPCs; and can stimulate an endogenous response in vivo, an effect that has proven elusive with biodegradable aAPCs. Accordingly, the present invention holds great promise to be clinically translatable as a rapid and effective immunotherapy, e.g., anti-cancer immunotherapy or anti-pathogenic immunotherapy, without the need for adoptive transfer.

In some embodiments, aAPCs are used to enrich and/or expand antigen-specific T cells ex vivo, for example, as disclosed in US 2017/0246277, which is hereby incorporated by reference in its entirety. aAPCs generally comprise one or more ligands that are an antigen presenting complex.

Antigen presenting complexes comprise an antigen binding cleft, which harbors an antigen for presentation to a T cell or T cell precursor. Antigen presenting complexes can be, for example, MHC class I or class II molecules, and can be linked or tethered to provide dimeric or multimeric MHC. In some embodiments, the MHC are monomeric, but their close association on the nano-particle is sufficient for avidity and T cell activation. In some embodiments, the MHC are dimeric. Dimeric MHC class I constructs can be constructed by fusion to immunoglobulin heavy chain sequences, which are then associated through one or more disulfide bonds (optionally with associated light chains). In some embodiments, the "signal 1" complex is a non-classical MHC-like molecule such as member of the CD1 family (e.g., CD1a, CD1b, CD1c, CD1d, and CD1e). MHC multimers can be created by direct tethering through peptide or chemical linkers, or can be multimeric via association with streptavidin through biotin moieties. In some embodiments, the antigen presenting complexes are MHC class I or MHC class II molecular complexes involving fusions with immunoglobulin sequences.

MHC class I molecular complexes having immunoglobulin sequences are described in U.S. Pat. No. 6,268,411, which is hereby incorporated by reference in its entirety. These MHC class I molecular complexes may be formed in a conformationally intact fashion at the ends of immunoglobulin heavy chains. MHC class I molecular complexes to which antigenic peptides are bound can stably bind to antigen-specific lymphocyte receptors (e.g., T cell receptors). In various embodiments, the immunoglobulin heavy chain sequence is not full length, but comprises an Ig hinge region, and one or more of CHI, CH2, and/or CH3 domains. The Ig sequence may or may not comprise a variable region, but where variable region sequences are present, the variable region may be full or partial. The complex may further comprise immunoglobulin light chains.

Exemplary MHC class I molecular complexes comprise at least two fusion proteins. A first fusion protein comprises a first MHC class I a chain and a first immunoglobulin heavy chain (or portion thereof comprising the hinge region), and a second fusion protein comprises a second MHC class I a chain and a second immunoglobulin heavy chain (or portion thereof comprising the hinge region). The first and second immunoglobulin heavy chains associate to form the MHC class I molecular complex, which comprises two MHC class I peptide-binding clefts. The immunoglobulin heavy chain can be the heavy chain of an IgM, IgD, IgG1, IgG3, IgG2, IgG2a, IgG4, IgE, or IgA. In some embodiments, an IgG heavy chain is used to form MHC class I molecular complexes. If multivalent MHC class I molecular complexes are desired, IgM or IgA heavy chains can be used to provide pentavalent or tetravalent molecules, respectively.

Exemplary class I molecules include HLA-A, HLA-B, HLA-C, and HLA-E, and these may be employed individually or in any combination. In some embodiments, the antigen presenting complex is an HLA-A2 ligand.

Exemplary MHC class II molecular complexes are described in U.S. Pat. Nos. 6,458,354, 6,015,884, 6,140,113, and 6,448,071, which are hereby incorporated by reference in their entireties. MHC class II molecular complexes comprise at least four fusion proteins. Two first fusion proteins comprise (i) an immunoglobulin heavy chain (or portion thereof comprising the hinge region) and (ii) an extracellular domain of an MHC class III chain. Two second fusion proteins comprise (i) an immunoglobulin κ or λ light chain (or portion thereof) and (ii) an extracellular domain of an MHC class Ha chain. The two first and the two second fusion proteins associate to form the MHC class II molecular complex. The extracellular domain of the MHC class III chain of each first fusion protein and the extracellular domain of the MHC class Ha chain of each second fusion protein form an MHC class II peptide binding cleft.

The immunoglobulin heavy chain can be the heavy chain of an IgM, IgD, IgG3, IgG1, IgG2, IgG2a, IgG4, IgE, or IgA. In some embodiments, an IgG1 heavy chain is used to form divalent molecular complexes comprising two antigen binding clefts. Optionally, a variable region of the heavy chain can be included. IgM or IgA heavy chains can be used to provide pentavalent or tetravalent molecular complexes, respectively.

Fusion proteins of an MHC class II molecular complex can comprise a peptide linker inserted between an immunoglobulin chain and an extracellular domain of an MHC class II polypeptide. The length of the linker sequence can vary, depending upon the flexibility required to regulate the degree of antigen binding and receptor cross linking.

In some embodiments, the HLA fusion construct contains no variable chain sequences. For example, the HLA or antigen presenting complex can be fused to an Ig constant region sequence above the hinge region to provide a dimeric HLA. For example, an HLA or antigen presenting portion thereof may be conjugated to a CHI portion of each IgG heavy chain. All IgG molecules consist of two identical heavy chains (constant and variable regions) joined together by disulfide bonds in the hinge region (upper and lower). For example, in some embodiments, an HLA molecule or antigen presenting complex is fused to the CHI (N-terminal end of the Ig H chain above the hinge region), thereby creating a dimeric fusion protein that is smaller due to lack of any VH and VL light chain sequences. Thus, such constructs would include CH2 and CH3 domains.

The antigen presenting complex may present a peptide antigen for activation of T cells (CD8+ or CD4+ T cells).

A variety of antigens can be bound to antigen presenting complexes. The nature of the antigens depends on the type of antigen presenting complex that is used. For example, peptide antigens can be bound to MHC class I and class II peptide binding clefts. Non-classical MHC-like molecules can be used to present non-peptide antigens such as phospholipids, complex carbohydrates, and the like (e.g., bacterial membrane components such as mycolic acid and lipoarabinomannan). Any peptide capable of inducing an immune response can be bound to an antigen presenting complex. Antigenic peptides include tumor-associated antigens, autoantigens, alloantigens, and antigens of infectious agents.

"Tumor-associated antigens" include unique tumor antigens expressed exclusively by the tumor from which they are derived, shared tumor antigens expressed in many tumors but not in normal adult tissues (oncofetal antigens), and tissue-specific antigens expressed also by the normal tissue from which the tumor arose. Tumor associated antigens can be, for example, embryonic antigens, antigens with abnormal post-translational modifications, differentiation antigens, products of mutated oncogenes or tumor suppressors, fusion proteins, or oncoviral proteins.

A variety of tumor-associated antigens are known in the art, and many of these are commercially available. Oncofetal and embryonic antigens include carcinoembryonic antigen and alpha-fetoprotein (usually only highly expressed in developing embryos but frequently highly expressed by tumors of the liver and colon, respectively), MAGE-1 and MAGE-3 (expressed in melanoma, breast cancer, and glioma), placental alkaline phosphatase sialyl-Lewis X (expressed in adenocarcinoma), CA-125 and CA-19 (expressed in gastrointestinal, hepatic, and gynecological tumors), TAG-72 (expressed in colorectal tumors), epithelial glycoprotein 2 (expressed in many carcinomas), pancreatic oncofetal antigen, 5T4 (expressed in gastriccarcinoma), alphafetoprotein receptor (expressed in multiple tumor types, particularly mammary tumors), and M2A (expressed in germ cell neoplasia).

Tumor-associated differentiation antigens include tyrosinase (expressed in melanoma) and particular surface immunoglobulins (expressed in lymphomas). Mutated oncogene or tumor-suppressor gene products include Ras and p53, both of which are expressed in many tumor types, Her-2/neu (expressed in breast and gynecological cancers), EGF-R, estrogen receptor, progesterone receptor, retinoblastoma gene product, myc (associated with lung cancer), ras, p53, nonmutant associated with breast tumors, MAGE-1, and MAGE-3 (associated with melanoma, lung, and other cancers). Fusion proteins include BCR-ABL, which is expressed in chromic myeloid leukemia. Oncoviral proteins include HPV type 16, E6, and E7, which are found in cervical carcinoma.

Tissue-specific antigens include melanotransferrin and MUC1 (expressed in pancreatic and breast cancers); CD10 (previously known as common acute lymphoblastic leukemia antigen, or CALLA) or surface immunoglobulin (expressed in B cell leukemias and lymphomas); the a chain of the IL-2 receptor, T cell receptor, CD45R, CD4+/CD8+ (expressed in T cell leukemias and lymphomas); prostate specific antigen and prostatic acid-phosphatase (expressed in prostate carcinoma); GP 100, MelanA/Mart-1, tyrosinase, gp75 brown, BAGE, and S-100 (expressed in melanoma); cytokeratins (expressed in various carcinomas); and CD19, CD20, and CD37 (expressed in lymphoma).

Tumor-associated antigens also include altered glycolipid and glycoprotein antigens, such as neuraminic acid-containing glycosphingolipids (e.g., GM2 and GD2, expressed in melanomas and some brain tumors); blood group antigens, particularly T and sialylated Tn antigens, which can be aberrantly expressed in carcinomas; and mucins, such as CA-125 and CA-19-9 (expressed on ovarian carcinomas) or the underglycosylated MUC-1 (expressed on breast and pancreatic carcinomas).

"Antigens of infectious agents" include components of protozoa, bacteria, fungi (both unicellular and multicellular), viruses, prions, intracellular parasites, helminths, and other infectious agents that can induce an immune response.

Bacterial antigens include antigens of gram-positive cocci, gram positive bacilli, gram-negative bacteria, anaerobic bacteria, such as organisms of the families Actinomycetaceae, Bacillaceae, Bartonellaceae, Bordetellae, Captophagaceae, Corynebacteriaceae, Enterobacteriaceae, Legionellaceae, Micrococcaceae, Mycobacteriaceae, Nocardiaceae, Pasteurellaceae, Pseudomonadaceae, Spirochaetaceae, Vibrionaceae and organisms of the genera *Acinetobacter, Brucella, Campylobacter, Erysipelothrix, Ewingella, Francisella, Gardnerella, Helicobacter, Levinea, Listeria, Streptobacillus* and *Tropheryma*.

Antigens of protozoan infectious agents include antigens of malarial plasmodia, *Leishmania* species, *Trypanosoma* species and *Schistosoma* species.

Fungal antigens include antigens of *Aspergillus, Blastomyces, Candida, Coccidioides, Cryptococcus, Histoplasma, Paracoccicioides, Sporothrix*, organisms of the order Mucorales, organisms inducing choromycosis and mycetoma and organisms of the genera *Trichophyton, Microsporum, Epidermophyton*, and *Malassezia*.

Viral peptide antigens include, but are not limited to, those of adenovirus, herpes simplex virus, papilloma virus, respiratory syncytial virus, poxviruses, HIV, influenza viruses, and CMV. Particularly useful viral peptide antigens include HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like.

Antigens, including antigenic peptides, can be bound to an antigen binding cleft of an antigen presenting complex either actively or passively, as described in U.S. Pat. No. 6,268,411, which is hereby incorporated by reference in its entirety. Optionally, an antigenic peptide can be covalently bound to a peptide binding cleft.

If desired, a peptide tether can be used to link an antigenic peptide to a peptide binding cleft. For example, crystallographic analyses of multiple class I MHC molecules indicate that the amino terminus of (32M is very close, approximately 20.5 Angstroms away, from the carboxyl terminus of an antigenic peptide resident in the MHC peptide binding cleft. Thus, using a relatively short linker sequence, approximately 13 amino acids in length, one can tether a peptide to the amino terminus of 132M. If the sequence is appropriate, that peptide will bind to the MHC binding groove (see U.S. Pat. No. 6,268,411).

In various embodiments, the particle (including and not limited to embodiments in which the particle is an aAPC) comprises a lymphocyte stimulatory or co-stimulatory molecule ("signal 2"). The stimulatory molecule may be a molecule that has a biological effect on a precursor T cell or on an antigen-specific T cell. Such biological effects include, for example, differentiation of a precursor T cell into a CTL, helper T cell (e.g., Th1, Th2), or regulatory T cell; and/or proliferation of T cells. Thus, T cell affecting molecules include T cell costimulatory molecules, adhesion molecules, T cell growth factors, and regulatory T cell inducer molecules. Such molecules include, but are not limited to, molecules that specifically bind to CD28 (including antibodies), CD80 (B7-1), CD86 (B7-2), B7-H3, 4-1BB, 4-1BBL, CD27, CD30, CD 134 (OX-40L), B7h (B7RP-1), CD40, LIGHT, antibodies that specifically bind to HVEM, antibodies that specifically bind to CD40L, antibodies that specifically bind to OX40, and antibodies that specifically bind to 4-1BB. In some embodiments, the costimulatory molecule (signal 2) is an antibody (e.g., a monoclonal antibody) or portion thereof, such as F(ab')2, Fab, scFv, or single chain antibody, or other antigen binding fragment. In some embodiments, the antibody is a humanized monoclonal antibody or portion thereof having antigen-binding activity, or is a fully human antibody or portion thereof having antigen-binding activity.

Non-limiting examples of T cell co-stimulatory pathways that can be targeted in these embodiments include the 4-1BB signaling pathway, the CD28 signaling pathway, the ICOS signaling pathway, the CD226 signaling pathway, the CRTAM signaling pathway, the TIM1 signaling pathway, the CD2 signaling pathway, the SLAM signaling pathway, the CD84 signaling pathway, the Ly9 signaling pathway, and the CRACC signaling pathway.

In some embodiments, signal 1 is provided by peptide-HLA-A2 complexes, and signal 2 is provided by B7.1-Ig or anti-CD28. An exemplary anti-CD28 monoclonal antibody is 9.3 mAb (Tan et al., *J. Exp. Med.* 1993 177: 165), which may be humanized in certain embodiments and/or conjugated to the bead as a fully intact antibody or an antigen-binding fragment thereof.

In some embodiments, the lymphocyte stimulatory or costimulatory molecule comprises one or more of CD80 (B7-1), CD86 (B7-2), a 4-1BB agonist such as 4-1BBL or an antibody against 4-1BB, an OX-40 agonist such as OX-40 or an antibody against OX-40, an ICOS agonist such as ICOS-L or antibody against ICOS, and a CD28 agonist such as an antibody against CD28. In some embodiments, the particle is an aAPC that provides a co-stimulatory signal (signal 2) that is an agonist for CD28, which is optionally a monoclonal antibody or antibody fragment.

In some embodiments, the particle comprises a ligand to redirect T cells (e.g., antigen-specific T cells) to tumors or cancer cells by presenting a ligand for a tumor or cancer cell surface marker. "Antigen-specific T cell Redirectors" (ATR) are particles comprising (A) at least one antibody that specifically binds to an antigen or epitope thereof present on a desired target cell and (B) at least one moiety that specifically binds antigen-specific effector T cells. ATRs are described in US 2015/0366991, which is hereby incorporated by reference in its entirety. ATR redirect the specific effector T cell population to the target cells, where the effector T cells mediate lysis of the target cells. An ATR also can include other molecules that have a biological effect on a precursor T cell or on an antigen-specific T cell. T cell affecting molecules include T cell costimulatory molecules, adhesion molecules. T cell growth factors, regulatory T cell inducer molecules, and apoptosis-inducing molecules.

Adhesion molecules useful for ATRs can be used to mediate adhesion of the ATR to a T cell or to a T cell precursor. Useful adhesion molecules include, for example, ICAM-1 and LFA-3.

In some embodiments, the ligand (which may be an antibody or fragment thereof) specifically binds to a tumor-associated antigen or epitope thereof. Tumor-associated antigens include unique tumor antigens expressed exclusively by the tumor from which they are derived, shared tumor antigens expressed in many tumors but not in normal adult tissues, and tissue-specific antigens expressed also by the normal tissue from which the tumor arose. Tumor-associated antigens can be, for example, embryonic antigens, antigens with abnormal post-translational modifications, differentiation antigens, products of mutated oncogenes or tumor suppressors, fusion proteins, or onco-viral proteins. Tumor-associated antigens also include altered glycolipid and glycoprotein antigens, such as neuraminic acid-containing glycosphingolipids (e.g., GM2 and GD2, expressed in melanomas and some brain tumors); blood group antigens, particularly T and sialylated Tn antigens, which can be aberrantly expressed in carcinomas; and mucins, such as CA-125 and CA-19-9 (expressed on ovarian carcinomas) or the underglycosylated MUC-1 (expressed on breast and pancreatic carcinomas).

Tissue-specific antigens include epithelial membrane antigen (expressed in multiple epithelial carcinomas), CYFRA 21-1 (expressed in lung cancer), Ep-CAM (expressed in pan-carcinoma), CA125 (expressed in ovarian cancer), intact monoclonal immunoglobulin or light chain fragments (expressed in myeloma), and the beta subunit of human chorionic gonadotropin (HCG, expressed in germ cell tumors).

In some embodiments, the redirector particles comprise ligands that bind to CD19, such as monoclonal antibodies (or fragments thereof) that bind to CD19. CD19 is useful for targeting B cell lymphomas, for example.

In some embodiments, the redirector particles comprise ligands that bind to her2, such as monoclonal antibodies (or fragments thereof) that bind to her2. Her2 is useful for targeting cancer cells, for example.

In some embodiments, the particles comprise one or more ligands that are lymphocyte activating molecules with an immune checkpoint blocking molecule. In some embodiments, the particle contains a ligand that targets (blocks) the immunosuppressive nature of the tumor microenvironment. Such particles are termed "immunoswitch" particles. Exemplary immune checkpoint blocking molecules include PD-1 (e.g., to sequester PD-1L signals), anti-PD-1, or anti-PD-1L, or an antagonist of PD-L2 (including monoclonal antibodies against PD-L2). In some embodiments, the immune checkpoint blocking molecule is anti-CTLA4. In some embodiments, one or more ligands are selected from an agonist for CD28, a 4-1BB agonist such as 4-1BBL or an antibody against 4-1BB, an OX-40 agonist such as OX-40 or an antibody against OX-40, and an ICOS agonist such as ICOS-L or antibody against ICOS.

Non-limiting examples of T cell co-stimulatory pathways that can be targeted in these embodiments include the 4-1BB signaling pathway, the CD28 signaling pathway, the ICOS signaling pathway, the CD226 signaling pathway, the CRTAM signaling pathway, the TIM1 signaling pathway, the CD2 signaling pathway, the SLAM signaling pathway, the CD84 signaling pathway, the Ly9 signaling pathway, and the CRACC signaling pathway.

In particular embodiments, the immune checkpoint protein is PD-L2. In some embodiments, the particle comprises a PD-L2 antagonist. In some embodiments, the PD-L2 antagonist comprises a monoclonal antibody against PD-L2 or an aptamer that targets PD-L2.

In particular embodiments, the particle comprises a CD73 antagonist antibody and a 4-1BB agonist antibody. In particular embodiments, the immunoswitch particle comprises a nanoparticle functionalized with both a CD73 antagonist antibody and a 4-1BB agonist antibody.

In some embodiments, the particle induces proliferation of NK cells. For example, the particle may comprise an OX-40 agonist such as anti-CD134 (OX40), a 4-1BB agonist such as anti-CD137 (4-1BB), or a both an OX-40 agonist and a 4-1BB agonist, such as anti-CD134 and anti-CD137.

As shown herein, the particles in accordance with this disclosure comprise ligands where about 0.0001% to about 1% of the mass of the particle comprises associated ligands. In some embodiments, the particles comprise ligands between 0.001% and 0.1% of the total mass of the particle.

In some embodiments, the particle further encapsulates a therapeutic or diagnostic agent. In such embodiments, the polymer blend may improve cellular delivery. Exemplary agents include polynucleotides, proteins, and peptides. For example, the particle may encapsulate cytokine(s) or growth factor(s), enzyme(s), therapeutic peptide(s), an mRNA, miRNA, an siRNA, or antisense oligonucleotide. T cell growth factors affect proliferation and/or differentiation of T cells. Examples of T cell growth factors include cytokines (e.g., interleukins, interferons) and superantigens. Particularly useful cytokines include IL-2, IL-4, IL-7, IL-10, IL-12, IL-15, and gamma interferon. T cell growth factors may be encapsulated in the beads or particles or chemically conjugated or adsorbed to the surface. Thus, in some embodiments, the nanoparticles further comprise a therapeutic compound or protein/peptide entrapped in the core of the particle (e.g. a chemotherapy agent, cytokine or interleukin such as IL-2, a chemokine like CCL9 that attracts T cells, and/or a checkpoint inhibitor molecule like anti-PD1 antibody or anti-PD1 peptide, or IDO inhibitor). In some embodiments, entrapped compounds are released by degradation of the particle matrix. Such an aAPC could make combination therapies more tolerable and efficacious by limiting unwanted activity due to off-target interactions. In some embodiments, the particle does not encapsulate any agent.

In other aspects, the invention provides pharmaceutical compositions comprising the particles as described herein and a pharmaceutically-acceptable excipient. The compositions can be formulated for administered to patients by any appropriate routes, including intravenous administration, intra-arterial administration, subcutaneous administration, intradermal administration, intralymphatic administration, and intra-tumoral administration. In some embodiments, the composition is lyophilized, and reconstituted prior to administration.

The particles and pharmaceutical compositions described herein are useful for immunotherapy, for example, in methods for activating immune cells or inducing the formation of antigen-specific cytotoxic T cells, either ex vivo or by administering an effective amount of the composition to a patient in need. In some embodiments, the patient is a cancer patient. In various embodiments described herein, the invention provides particle-based platforms for activating immune cells, such as T cells, B cells, natural killer cells, or dendritic cells.

In some embodiments, particles (e.g., aAPCs or particles for expanding NK cells) are contacted with lymphocytes from the patient or an HLA-matched donor, such that target lymphocytes are expanded ex vivo. For example, cells can be expanded in culture for about 1 to about 4 weeks (e.g., about 2, 3, or 4 weeks). An exemplary source of lymphocytes is PBMCs, which may be enriched for a variety of cell types prior to expansion of cells, including CD4+ cells, CD8+ cells, NK cells, or B cells). In other embodiments, the immune cell is contacted in vivo by administration of the particles to the patient.

In various embodiments, the invention provides methods for treating a disease or disorder, including but not limited to cancer, in a subject comprising administering to the subject the particles or compositions described herein. The particles may be administered via intravenous administration, intra-arterial administration, subcutaneous administration, intralymphatic administration, or intra-tumoral administration. In some embodiments, the particles are administered by intratumoral injection. The subject may be a human or animal patient.

In some embodiments, the cancer is a hematological malignancy, or is a solid tumor, such as a carcinoma or sarcoma. In embodiments, the cancer is selected from breast, lung, glioblastoma, renal cell, hepatic cell, head, and neck cancer. In embodiments the cancer is a solid tumor cancer selected from germ line tumors, tumors of the central nervous system, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma (including advanced melanoma), renal cancer, bladder cancer, esophageal cancer, cancer of the larynx, cancer of the parotid, cancer of the biliary tract, rectal cancer, endometrial cancer, squamous cell carcinomas, adenocarcinomas, small cell carcinomas, neuroblastomas, mesotheliomas, adrenocortical carcinomas, epithelial carcinomas, desmoid tumors, desmoplastic small round cell tumors, endocrine tumors, Ewing sarcoma family tumors, germ cell tumors, hepatoblastomas, hepatocellular carcinomas, lymphomas, non-rhabdomyosarcome soft tissue sarcomas, osteosarcomas, peripheral primative neuroectodermal tumors, retinoblastomas, rhabdomyosarcomas, and Wilms tumors.

In some embodiments, the disease is an infectious disease, such as viral, fungal, bacterial, or parasitic infection, whereby CD8+ and/or CD4+ cells are activated and expanded, or particles are administered directly to the patient.

In some embodiments, the particles activate and expand regulatory T cells in vivo or ex vivo, for treatment of an autoimmune disorder.

Unless specifically stated or obvious from context, as used herein, the term "about" is understood as within a range of normal tolerance in the art, for example, within plus or minus 10%.

This invention is further illustrated by the following non-limiting examples.

EXAMPLES

Example 1: Exemplary Methods for Preparing PLGA and PLGA/PBAE Microspheres

PLGA-only (control) microparticles and microparticles comprising PLGA and PBAE were prepared by single emulsion. Briefly, PBAEs (of Structure 3) were synthesized by polymerizing a base chain diacrylate group and a hydroxyl amine in solvent free conditions at 90° C. See FIG. 7. The terminal acrylate groups on the resulting PBAE were end capped with an amine coupled functional group to enhance the PBAE efficacy. PLGA (50:50)/PBAE particles were synthesized by single emulsion at a 3:1 PLGA:PBAE ratio. The microparticles were washed and lyophilized. The lyophilized microparticles were then functionalized using EDC/NHS (1-ethyl-3-(3-dimethylaminopropyl)carbodiimide hydrochloride/N-hydroxysuccinimide) chemistry to attach the two signals for CD8+ T cell activation to the microparticles. $K^b$-SIY peptide-MHC dimer (as Signal 1) and anti-CD28 monoclonal antibody (mAb) (as Signal 2), were conjugated at a 1:1 ratio on the surface of both PLGA-only microparticles and PLGA/PBAE microparticles.

Figure 1A:
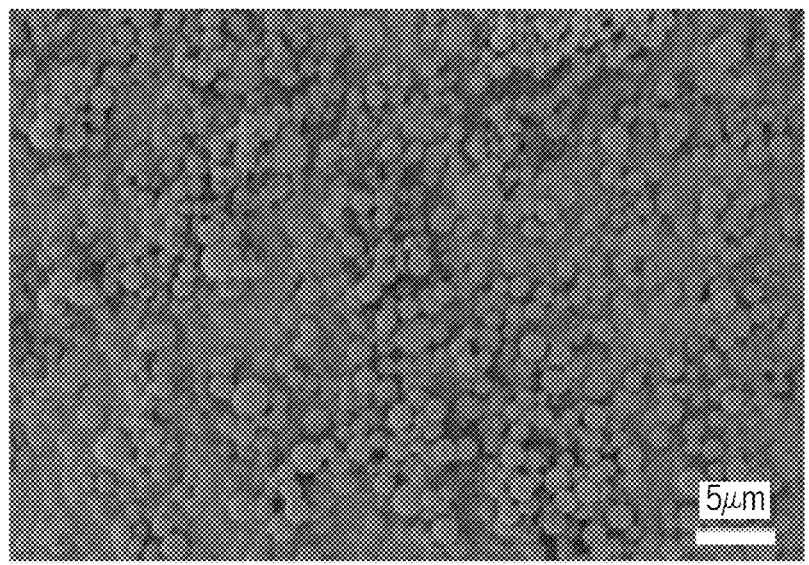
FIG. 1A and FIG. 1B show scanning electron microscope (SEM) images of microparticles synthesized by single emulsion comprising poly(lactic-co-glycolic acid) (PLGA) (FIG. 1A) and comprising PLGA and poly(beta-amino ester) (PBAE) (FIG. 1B).
Figure 1B:
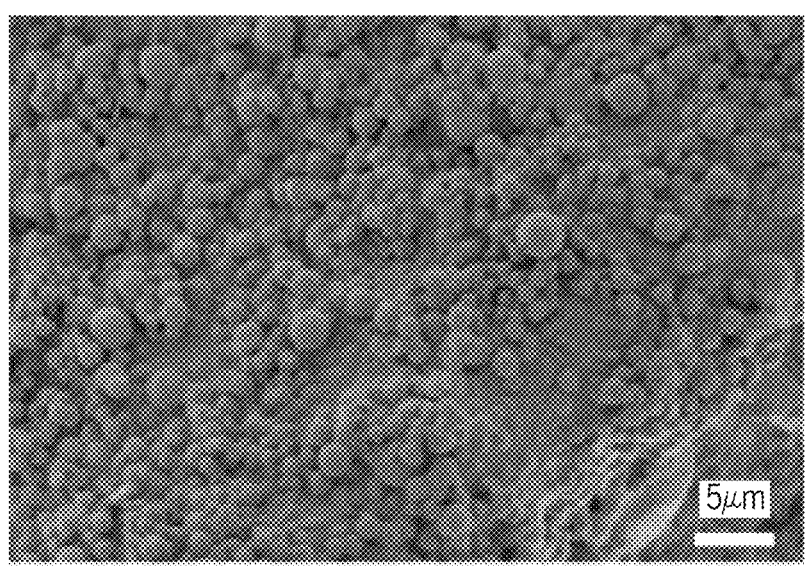
Figure 1C:
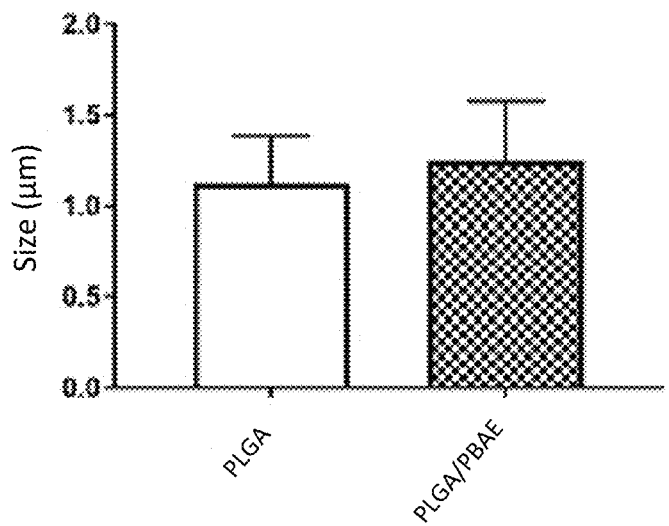
FIG. 1C shows average size and standard error for one hundred representative particles of each microparticle type.
Figure 1D:
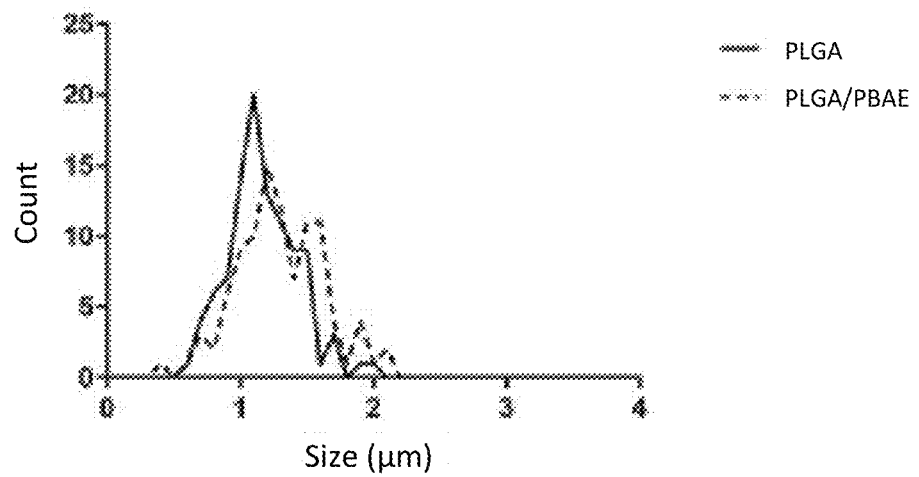
FIG. 1D shows size distributions for particles of each microparticle type.

The PLGA microparticles and the PLGA/PBAE microparticles were characterized using scanning electron microscopy (SEM). Morphologically, the two types of microparticles were identical in surface features and spherical shape (FIG. 1A and FIG. 1B). The microparticle sizes were determined using ImageJ analysis of the SEM micrographs; the sizes of the two types of microparticles were statistically similar (n=100; FIG. 1C). Additionally, size distributions were essentially identical between the two microparticle types (FIG. 1D).

Figure 1E:
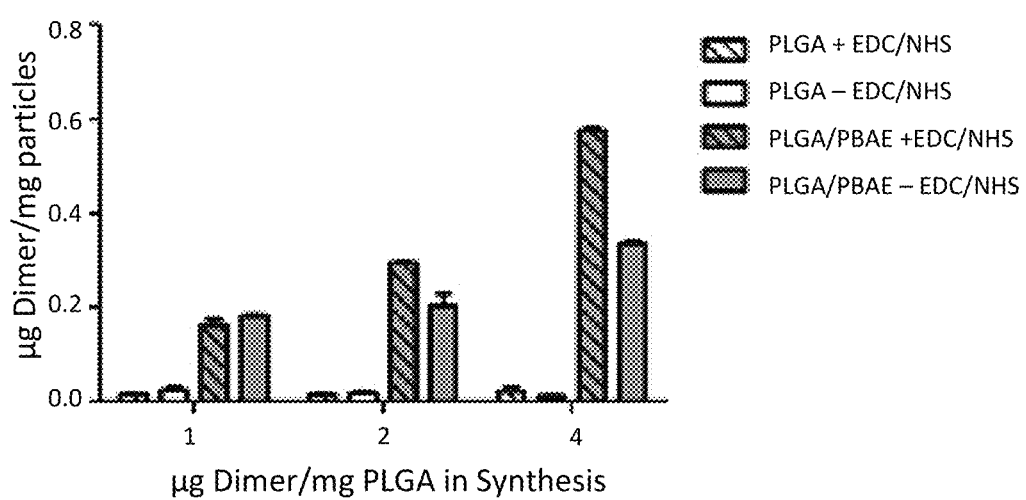
FIG. 1E shows protein conjugation efficacy (MHC-Ig dimers) for PLGA and PLGA/PBAE microparticles (i.e., artificial antigen presenting cells (aAPCs)) with or without EDC/NHS (1-ethyl-3-(3-dimethylaminopropyl)carbodiimide hydrochloride/N-hydroxysuccinimide) conjugation reagents.

To characterize the amount of protein immobilized on the surface of the microparticles, Signal 1 protein and Signal 2 protein, each of which was fluorophore-conjugated, were combined with the microparticles of the present invention and the fluorescence associated with the microparticle (after protein conjugation) as assessed (FIG. 1E). The PLGA/PBAE microparticles immobilized a significantly higher amount of protein after functionalization ("PLGA/PBAE+EDC/NHS") compared to the functionalized PLGA microparticles ("PLGA+EDC/NHS"); also, a large fraction of the protein was bound non-specifically in the absence of conjugation reagents ("PLGA/PBAE-EDC/NHS" and "PLGA-EDC/NHS").

Furthermore, these experiments demonstrate that when PLGA/PBAE aAPC microparticles (P/B) and PLGA aAPC microparticles were fabricated under the same conditions, the PLGA/PBAE aAPC microparticles (P/B) had a greater amount of protein on their surfaces (i.e., Signal 1 Dimer and Signal 2 aCD28). (FIG. 8) The cationic nature of the PBAE polymer blended with the non-cationic PLGA polymer allowed for this increase in protein surface density.

Example 2: PLGA/PBAE Microparticles (aAPCs) Bind to and Activate Cognate CD8+ T Cells In this example, the stimulatory potential of the PLGA/PBAE microparticles (aAPCs) on antigen-specific CD8+ T cells was determined.

CD8+ T cells from a 2C transgenic mouse recognize the $K^b$-SIY peptide MHC complex. Thus, this complex is useful for studying CD8+ T cell activation potential in vitro.

Figure 2A:
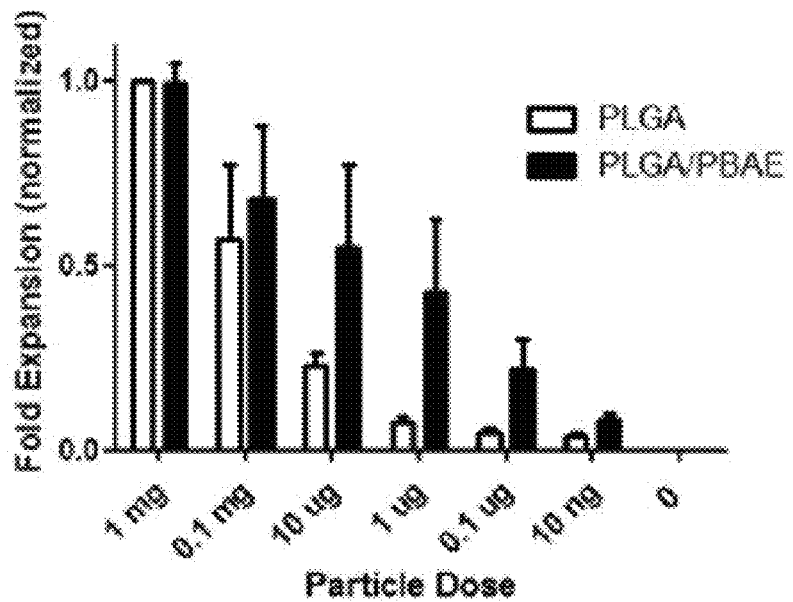
FIG. 2A is a graph showing the relative expansion of 2C CD8+ T cells incubated with $K^b$-SIY/anti-CD28-comprising PLGA aAPC or with $K^b$-SIY/anti-CD28-comprising PLGA/PBAE aAPC, normalized to 1 mg PLGA. Significance is by two-way ANOVA (p<0.05).
Figure 2B:
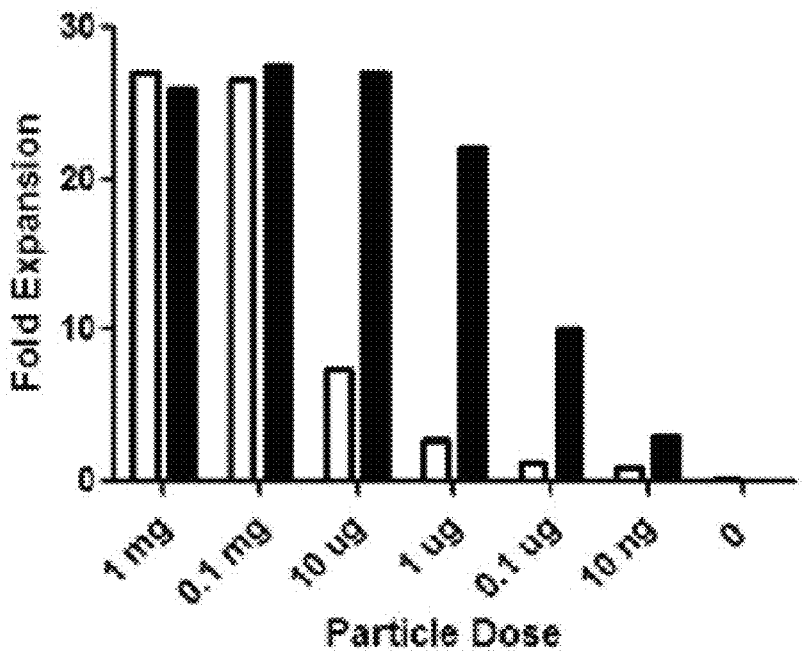
FIG. 2B is a graph showing representative total expansion of 2C CD8+ T cells incubated with the above-mentioned PLGA aAPCs or with the above-mentioned PLGA/PBAE aAPCs.

Here, the CD8+ T cells from the 2C transgenic mouse were contacted with PLGA aAPCs and PLGA/PBAE aAPCs, each functionalized with the $K^b$-SIY peptide MHC complex. As shown in FIG. 2A and FIG. 2B, both aAPCs stimulated expansion of 2C CD8+ T cells; however, the PLGA/PBAE aAPCs stimulated equivalent expansion of 2C CD8+ T cells at a 100× lower dose than the PLGA-only aAPCs.

Figure 2C:
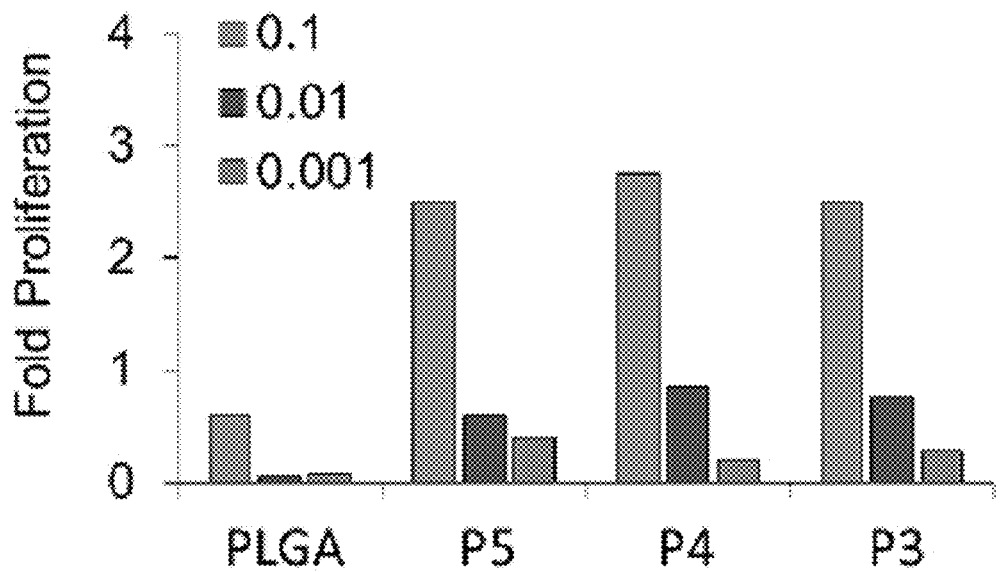
FIG. 2C is a graph showing relative proliferation (i.e., expansion) of T cells incubated with aAPCs comprising PBAE containing a 5, 4, or 3 carbon chain backbone (P4, P5, and P3, respectively) and at varying doses (0.1, 0.01, and 0.001 mg aAPC).

Consequences on the stimulatory potential of PLGA/PBAE microparticles from various lengths of the carbon chain in the PBAE backbone were then assayed. Here, PBAE backbones with three-, four-, or five-carbon length chains were prepared and used in functionalized PLGA/PBAE aAPCs. As shown in FIG. 2C, varying the length of the carbon chain had little to no effect on CD8+ T cell activation (i.e., proliferation) across three doses. In embodiments of the present invention, PBAE backbones with four-carbon length chains were preferentially used.

The relative amount of PBAE in a microparticle, in part, determines the biodegradation rate and siRNA encapsulation ability of a PLGA/PBAE microparticle. Thus, microparticles having differing PBAE ratios may have different characteristics and uses, e.g., siRNA encapsulation and in vivo kinetics. Thus, the effects on T cell activation from various ratios of PBAE in a PLGA/PBAE microparticle were then investigated.

Figure 2D:
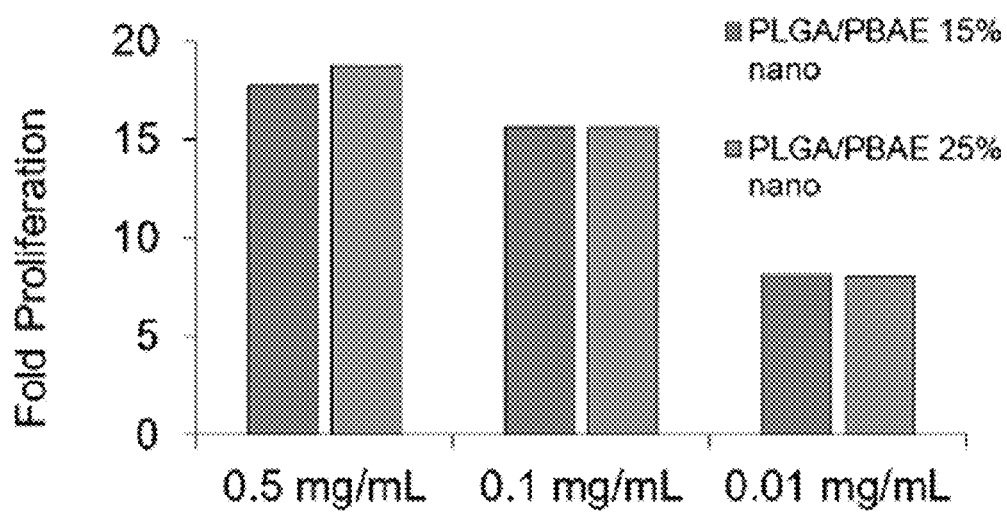
FIG. 2D is a graph showing relative proliferation (i.e., expansion) of T cells incubated with aAPCs comprising varying percentages of PBAE.

Here, PLGA/PBAE microparticles containing 25% PBAE (i.e., a 3:1 PLGA to PBAE ratio) were compared to microparticles containing 15% PBAE (i.e., a 17:3 PLGA to PBAE ratio). As shown in FIG. 2D, the CD8+ T cell stimulatory potential was unchanged based upon the PBAE content of the microparticle. These data show that PLGA/PBAE microparticles are robust stimulators of cognate CD8+ T cell responses and are relatively insensitive to PBAE construct and concentration.

Figure 3A:
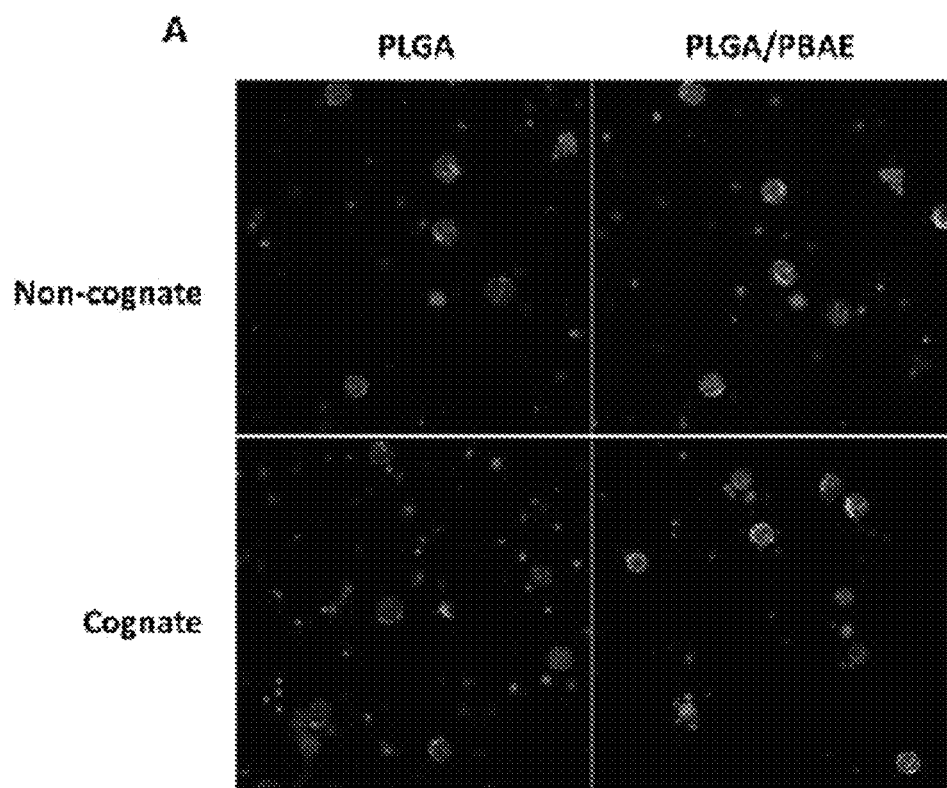
FIG. 3A includes confocal images showing PLGA/PBAE aAPC (red) bind cognate cells (green) at a higher frequency than PLGA aAPC (red).
Figure 3B:
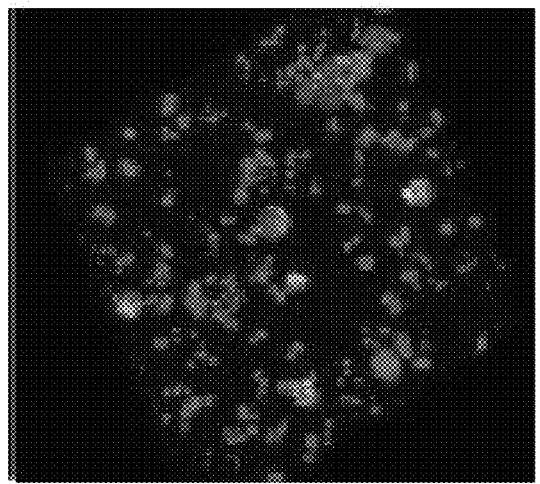
FIG. 3B is a three-dimensional reconstruction of a plurality of confocal images.
Figure 3B:
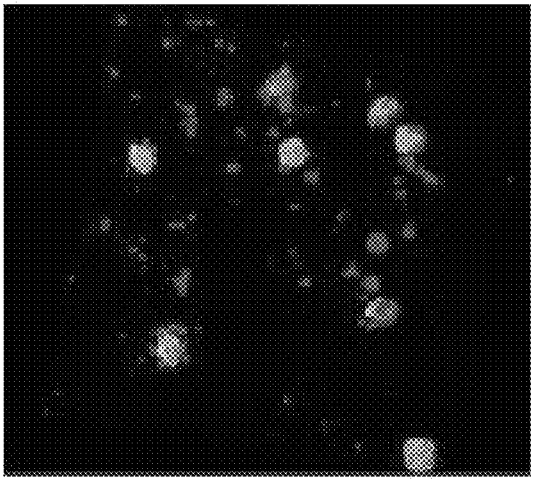

To further study how well the PLGA/PBAE microparticles interact with cells of interest, confocal microscopy and flow cytometry experiments were performed using aAPCs that encapsulate a fluorescent dye. As shown in the confocal micrographs of FIG. 3A, PLGA/PBAE aAPCs bind cognate but not non-cognate CD8+ T cells. As shown by three-dimensional reconstructed images (FIG. 3B), PLGA/PBAE aAPCs bind cognate cells at a higher frequency than PLGA-only aAPCs. The superior binding PLGA/PBAE aAPCs relative to PLGA-only aAPCs was confirmed by flow cytometry. As shown in FIG. 3C, neither aAPC type had significant binding to non-cognate cells. However, the PLGA/PBAE aAPCs bound more cognate cells and at a higher level than the PLGA-only aAPCs.

These data demonstrate that PLGA/PBAE aAPCs specifically bind cognate cells at a higher level than PLGA-only aAPC and PLGA/PBAE aAPCs are able to stimulate a specific cognate CD8+ T cell response at 10 to 100× lower doses than PLGA-only aAPCs.

Example 3: PLGA/PBAE aAPCs Inhibit Tumor Growth In Vitro and In Vivo

In this example, the ability of PLGA/PBAE aAPCs to inhibit tumor growth in vitro and in vivo and increase survival of tumor-bearing animals was assayed.

PLGA/PBAE aAPCs were synthesized as described above and were functionalized with $K^b$-trp2 and $D^b$-gp100 (as Signal 1) and anti-CD28 mAb (as Signal 2). Wild type C57BL/6 mice (n=6 per group) were injected with 3×10⁵ B16-F10 cells, which express $K^b$-trp2 and $D^b$-gp100, subcutaneously on day 0. On days 4, 11, and 18, half the mice were intravenously treated with 2 mg functionalized PLGA/PBAE aAPC.

Figure 4A:
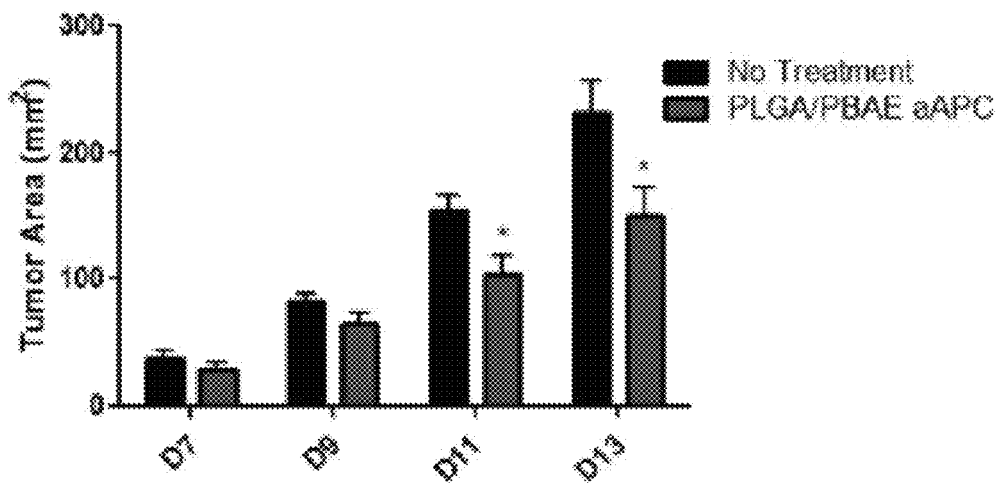
FIG. 4A is a graph showing that in vivo PLGA/PBAE aAPC treatment inhibits growth of established B16-F10 tumors.
Figure 4B:
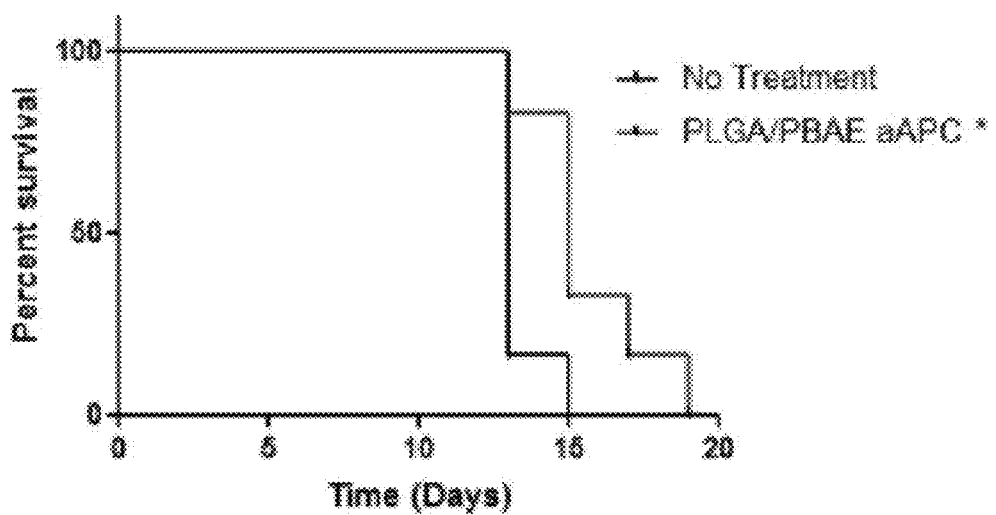
FIG. 4B is a graph showing that in vivo treatment extends survival of mice carrying B16-F10 tumors.

All mice, including the non-treated group, received 200 μg on day 4 and 100 μg of anti-PD-1 monoclonal antibody on day 5. This is a dose which has no effect on tumor growth when given as a monotherapy (data not shown). As shown in FIG. 4A, mice that received the functionalized PLGA/PBAE aAPC injection had significantly delayed tumor growth. Importantly, mice that received the functionalized PLGA/PBAE aAPC injection lived significantly longer; with non-treated mice dying at day 13, on average, whereas the aAPC-treated mice died, on average, at day 16 (See, FIG. 4B).

The PLGA/PBAE aAPC microparticles could also expand the endogenous repertoire of T cells ex vivo (FIG. 9). In addition, when PLGA/PBAE aAPC microparticles were administered either intravenously (blue/green) or intralymph node (purple) to mice bearing melanoma tumors, the PLGA/PBAE aAPC microparticles were able to stimulate endogenous cytotoxic T cells to attack and decrease the growth of the melanoma tumor. (FIG. 10) No adoptive transfer of T cells was required with the PLGA/PBAE aAPC microparticles to have an anti-tumor effect at a distant tumor site.

The data demonstrate that the PLGA/PBAE aAPCs of the present invention have greater CD8+ T cell stimulatory potential than its PLGA-only aAPCs. These new aAPCs can stimulate an endogenous response in vivo which has not previously been observed with biodegradable aAPCs. Finally, the new aAPCs specifically bind cognate cells at a higher frequency and activate cells in vitro at about a 100× lower doses than PLGA-only aAPCs.

Accordingly, functionalized PLGA/PBAE aAPCs of the present invention are useful for treating cancer in vivo and without adoptive transfer of ex vivo-activated and expanded tumor-specific T cells.

Example 4: PLGA/PBAE Microparticles Bind to and Stimulate NK Cells

In this example, the stimulatory potential of the PLGA/PBAE microparticles on Natural killer (NK) cells was assayed.

Natural killer (NK) cells selectively destroy tumor cells without requiring antigen specificity. These characteristics make NK cells a valuable tool in cancer immunotherapy. However, immunosuppressive cues present in a tumor's microenvironment decrease NK cell activity; these cues limit the ability of NK cells to recognize and destroy cancerous cells (Vitale M, et al., *Eur J Immunol*, 2014). Anti-cancer therapies which restore NK cell cytotoxic abilities may be promising solutions.

Adoptive NK cell therapies have shown success in a variety of murine cancer models; however, these therapies are costly, restricted in scalability, and are currently limited to cellular aAPC platforms. Below is described an alternative strategy, which uses a novel particle-based system having the ability to expand NK cell populations in vitro.

Figure 5A:
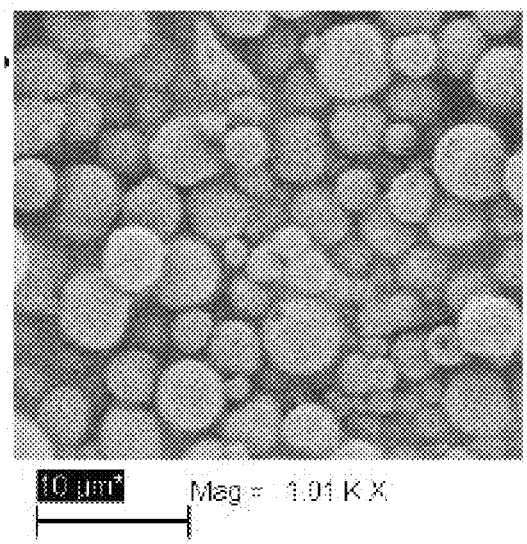
FIG. 5A and FIG. 5B show scanning electron microscope (SEM) images of microparticles synthesized by single emulsion comprising PLGA (FIG. 5A) and comprising PLGA/PBAE (FIG. 5A).
Figure 5B:
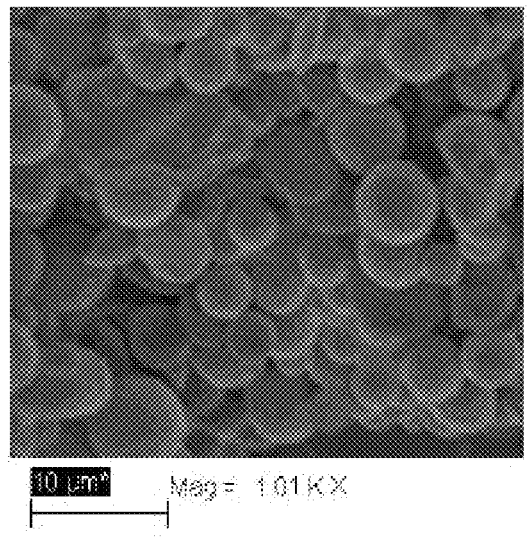

Poly (beta-amino ester) (PBAE) was synthesized according to the method described in Meyer R, et al. *JBMR Part A*, 2015. Microparticles were fabricated from poly (lactic-co-glycolic acid) (PLGA) or a blend of PLGA and PBAE using a single emulsion technique. Using EDC/NHS chemistry, the microparticles were functionalized with an anti-CD134 monoclonal antibody (OX40), an anti-CD137 monoclonal antibody (4-1BB), or a combination of both monoclonal antibodies (4-1BB+OX40). Following synthesis, scanning electron microscopy images PLGA microparticles (FIG. 5A) and PLGA/PBAE (FIG. 5B) microparticles confirmed the similar size and morphology of the two types of microparticles.

Figure 5C:
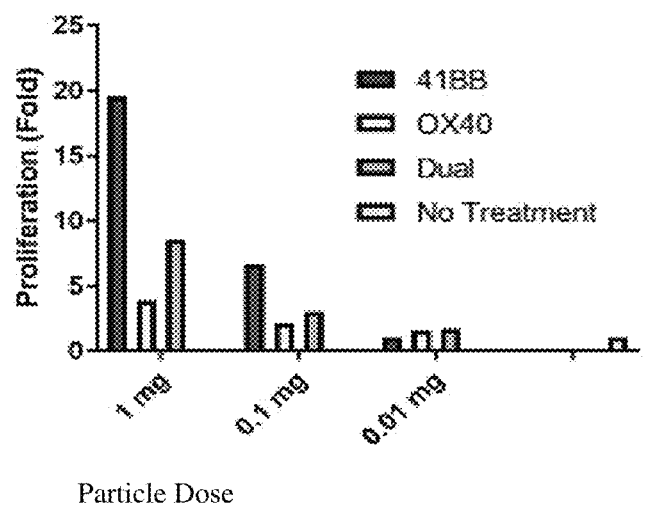
FIG. 5C is a graph showing in vitro Natural killer (NK) cell proliferation mediated by 4-1BB-comprising particles is stronger than OX40-comprising particles and 4-1BB and OX40-comprising particles (dual).

To evaluate the ability of different surface-conjugated proteins to stimulate NK cells in vitro, NK cells were isolated from B6 mice and incubated, in the presence of IL-2, with 4-1BB-, OX40-, or 4-1BB+OX40-functionalized microparticles. After 7 days, NK cells were manually counted to assess proliferation. In a microparticle dose-dependent manner, NK cells incubated with 4-1BB-functionalized microparticles had stronger NK cell proliferation than NK cells incubated with OX40-functionalized microparticles or with 4-1BB+OX40-functionalized microparticles (FIG. 5C).

Figure 5D:
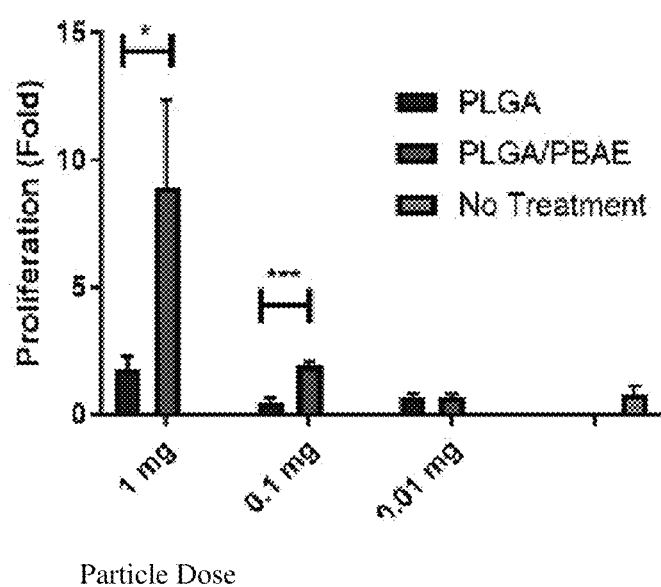
FIG. 5D is a graph showing that PLGA/PBAE particles provide higher NK cell proliferation than PLGA particles. Statistical test performed is one-way ANOVA at each dose with Tukey's post-test. (*=p<0.05, =p<0.01, and *=p<0.001).

To investigate the effects of polymer type on the ability of particles to expand NK cell populations, NK cells were isolated and cultured, in the presence of various IL-2 concentrations, with PLGA and PLGA/PBAE microparticles functionalized with the anti-4-1BB monoclonal antibody. At the end of 3 days, NK cell proliferation was assessed. NK cells cultured with the PLGA/PBAE microparticles showed an approximately 4.5-fold increase in proliferation over NK cells cultured with the PLGA microparticles (FIG. 5D). Varying the concentration of soluble IL2 from 50 to 1000 U/mL did not significantly affect NK cell proliferation.

These data demonstrate a novel microparticle-based method using an antibody functionalized PLGA/PBAE microparticles to effectively expand NK cell populations in vitro. Accordingly, microparticles show potential as a platform for NK cell-mediated cancer immunotherapy.

Example 5: PLGA/PBAE Microparticles can be Designed to Act as an "Immunoswitch"

In this example, the ability of PLGA/PBAE microparticles to act as an "Immunoswitch" was tested.

Here, PLGA/PBAE microparticles were functionalized with proteins on their surfaces which produced microparticles that are useful for applications separate from and in addition to acting as an aAPCs.

For example, certain PLGA/PBAE microparticles are able to act as an "immunoswitch" particle to stimulate immune cells and cause release of IFN-gamma.

Figure 6:
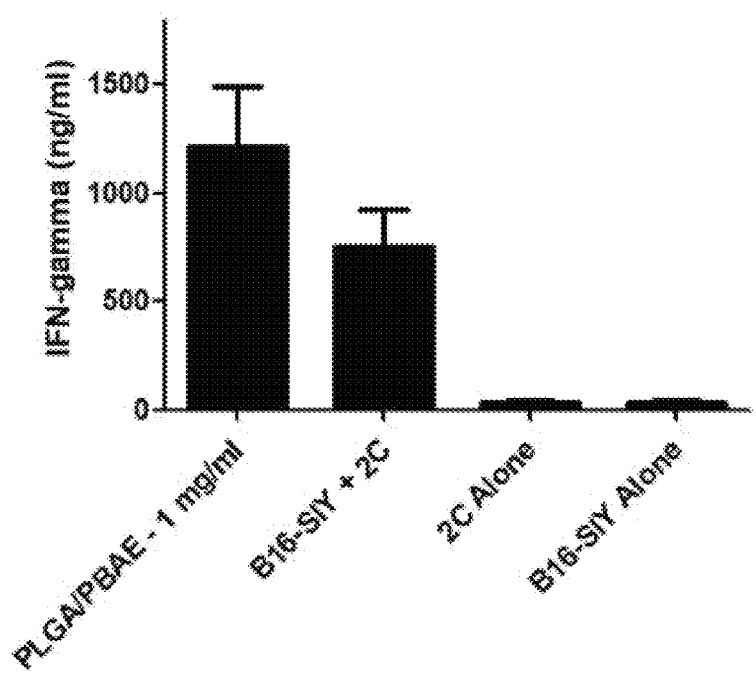
FIG. 6 is a graph showing biomimetic particles of the present invention work as "immunoswitch" particles to stimulate immune cells and cause release of IFN-gamma.

FIG. 6 is a graph showing biomimetic particles of the present invention work as "immunoswitch" particles to stimulate immune cells and cause release of IFN-gamma. Immunoswitch particles combine agonistic anti-4-1BB monoclonal antibodies and antagonistic anti-PD-L1 monoclonal antibodies on the surface of nanoparticles. The efficacy of iron-dextran-based immunoswitch particles has been demonstrated in their ability to induce CD8+ T cell activation when co-incubated with cognate tumor cells. To study the ability of PLGA/PBAE to serve as a platform for immunoswitch particles, immunoswitch particles were constructed from PLGA/PBAE and co-incubated with 2C CD8+ T cells and cognate B16-SIY tumor cells. PLGA/PBAE particles were added to culture at doses ranging from 0.001-1 mg particles/ml. IFN-γ release was measured.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

Claim 9, Column 24, Line 48-49 should read:
9. The particle of claim 6, wherein R" comprises an end group having the structure E7:
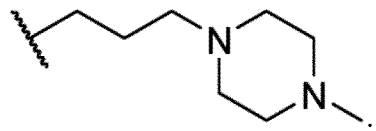

What is claimed is:

1. A particle comprising a polymer blend of a polyester comprising one or more of poly(lactic-co-glycolic acid) (PLGA), polyglycolic acid (PGA), and polylactic acid (PLA) and a poly(beta-amino ester) (PBAE), the particle comprising, on its surface, one or more ligands for one or more cell surface receptor(s) or cell surface molecule(s), wherein the particle comprises a ratio of polyester to polyamine selected from the group consisting of from about 8:1 to about 2:1; from about 6:1 to about 3:1; about 2:1, about 3:1, about 4:1, about 5:1, about 6:1, and about 7:1.

2. The particle of claim 1, wherein the polyester is poly(lactic-co-glycolic acid) (PLGA), and the polyamine is poly(beta-amino ester) (PBAE).

3. The particle of claim 1, comprising a polymer blend of PLGA (50/50) and PBAE.

4. The particle of claim 1, wherein the particle has an average diameter selected from the group consisting of from about 1 micron to about 5 microns; from about 50 nm to about 1 micron; and from about 50 nm to about 500 nm.

5. The particle of claim 1, wherein the particle is from about 10% to about 50% polyamine.

6. The particle of claim 5, wherein the polyamine is PBAE having the structure of:

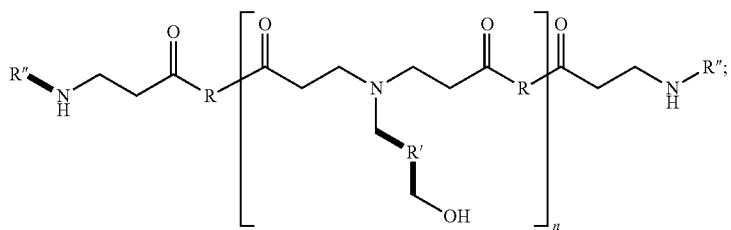

(Structure I)

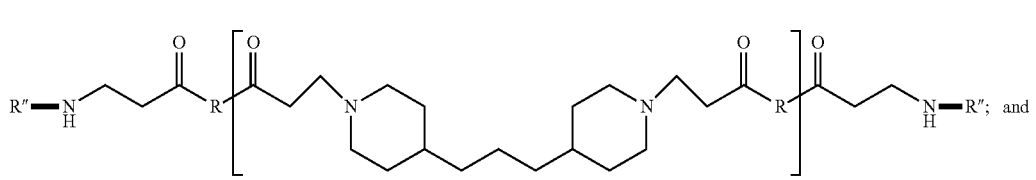

(Structure II); and

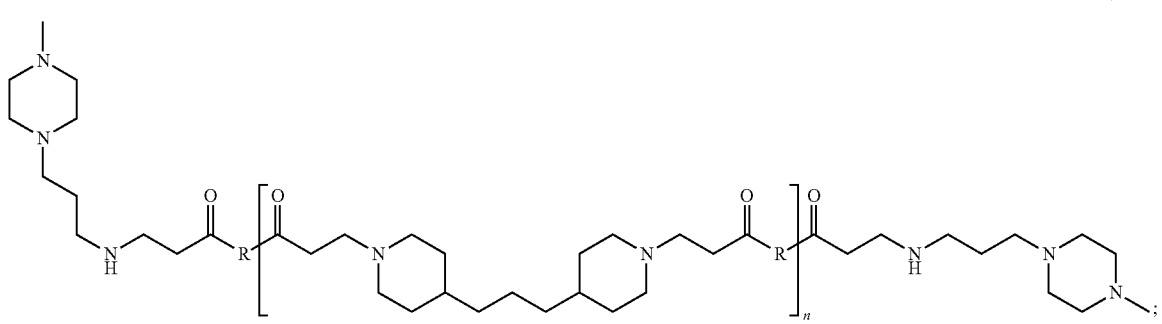

(Structure III)

where n is an integer of from 1 to 10,000;
- R comprises a backbone of a diacrylate selected from one or more of:
- R together with a group to which it is attached forms a linear or branched C3 to C7 diester;
- R' is a side chain comprising a C1 to C8 linear or branched alkylene, which is optionally substituted with substituent group selected from hydroxyl, alkyl, alkenyl, thiol, amine, carbonyl, and halogen; and
- R" is an end group comprising one or more primary, secondary or tertiary amines.

7. The particle of claim 6, wherein R" comprises an aromatic or non-aromatic carbocyclic or heterocyclic group having 5 or 6 atoms.

8. The particle of claim 6, wherein R" comprises one or more ether, thioether, or disulfide linkages.

9. The particle of claim 6, wherein R" comprises an end group having the structure E7.

10. The particle of claim 6, wherein the polyester is poly(lactic-co-glycolic acid) (PLGA), and the polyamine is a poly(beta-amino ester) (PBAE) having structure III:

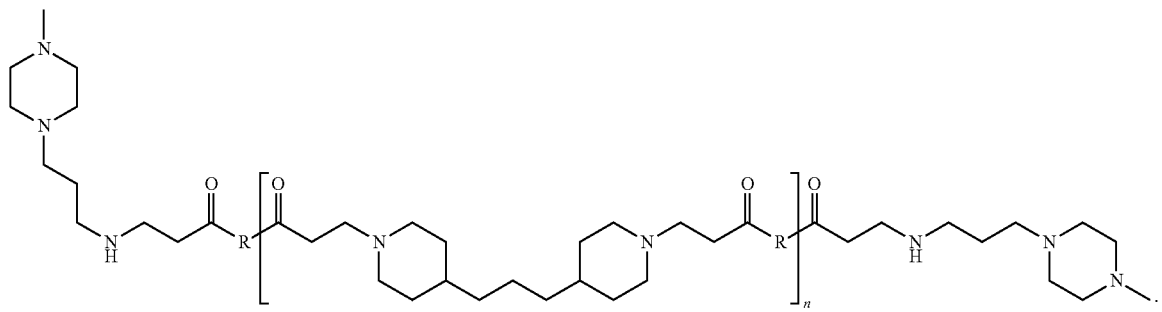

11. The particle of claim 1, wherein the particle is an artificial antigen presenting cell (aAPC).

12. The particle of claim 11, wherein the one or more ligands comprise an antigen presenting complex.

13. The particle of claim 12, wherein the antigen presenting complex is an MHC class I molecular complex or an MHC class II molecular complex or wherein the antigen presenting complex presents a peptide antigen for activation of T cells.

14. The particle of claim 1, wherein the one or more ligands comprise a molecule selected from the group consisting of a lymphocyte stimulatory molecule, a co-stimulatory molecule, a lymphocyte activating molecule, and an immune checkpoint blocking molecule.

15. The particle of claim 14, wherein the particle targets a T cell co-stimulatory pathway selected from the 4-1BB signaling pathway, the CD28 signaling pathway, the ICOS signaling pathway, the CD226 signaling pathway, the CRTAM signaling pathway, the TIM1 signaling pathway, the CD2 signaling pathway, the SLAM signaling pathway, the CD84 signaling pathway, the Ly9 signaling pathway, and the CRACC signaling pathway.

16. The particle of claim 14, wherein the lymphocyte stimulatory or costimulatory molecule comprises one or more of CD80 (B7-1), CD86 (B7-2), a 4-1BB agonist or an antibody against 4-1BB, an OX-40 agonist or an antibody against OX-40, an ICOS agonist or antibody against ICOS, and a CD28 agonist.

17. The particle of claim 16, wherein the one or more ligands comprise an agonist for CD28, which is optionally a monoclonal antibody or antibody fragment.

18. The particle of claim 14, wherein the immune checkpoint blocking molecule is selected from the group consisting of PD-1, anti-PD-1, anti-PD-1L, anti-PD-L2, and anti-CTLA4.

19. The particle of claim 1, comprising a ligand against a tumor or cancer cell surface marker, which is optionally CD19 or her2, and an antigen presenting complex.

20. The particle of claim 1, wherein the particle comprises an OX-40 agonist, a 4-1BB agonist, or both an OX-40 agonist and a 4-1BB agonist.

21. The particle of claim 20, wherein the OX-40 agonist comprises anti-CD134 (OX40) and the 4-1BB agonist comprises anti-CD137 (4-1BB).

22. The particle of claim 1, wherein about 1% to about 10% of the mass of the particle comprises associated ligands.

23. The particle of claim 1, wherein the particle encapsulates a molecule selected from the group consisting of polynucleotide, protein, peptide, a cytokine or growth factor, enzyme, mRNA, miRNA, siRNA, and an antisense oligonucleotide.

24. The particle of claim 1, wherein the ligands are conjugated to the particle surface, optionally with EDC-NHS chemistry.

25. A pharmaceutical composition comprising a particle of claim 1 and a pharmaceutically-acceptable excipient.

26. A method for activating an immune cell comprising contacting the immune cell or tumor microenvironment with a particle of claim 1.

27. The method of claim 26, wherein the particle and immune cell are contacted ex vivo or the immune cell or tumor microenvironment is contacted in vivo by injection of the particles.

28. The method of claim 27, wherein the immune cell is a T cell, B cell, natural killer cell, or dendritic cell.

29. The method of claim 27, wherein the particle is an aAPC, and target lymphocytes are enriched and/or expanded ex vivo.

30. A method for treating a disease or disorder in a subject comprising administering to the subject a particle of claim 1.

31. The method of claim 30, wherein the particle is administered via intravenous administration, intra-arterial administration, subcutaneous administration, intralymphatic administration, or intra-tumoral administration.

32. The method of claim 30, wherein the subject is human.

33. The method of claim 30, wherein the condition comprises is selected from the group consisting of a cancer, an infectious disease, and an autoimmune disease.

34. The method of claim 33, wherein the cancer is a hematological malignancy, carcinoma, or sarcoma.

* * * * *

UNITED STATES PATENT AND TRADEMARK OFFICE
CERTIFICATE OF CORRECTION

PATENT NO. : 12,059,476 B2
APPLICATION NO. : 16/754951
DATED : August 13, 2024
INVENTOR(S) : Jordan J. Green et al.

Page 1 of 2

It is certified that error appears in the above-identified patent and that said Letters Patent is hereby corrected as shown below:

In the Claims

Claim 6, Column 23, Line 43-44 should read
R comprises a backbone of a diacrylate selected from one or more of:

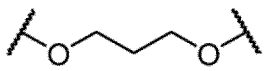

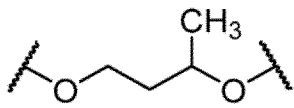

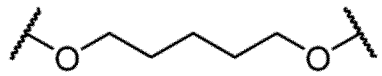

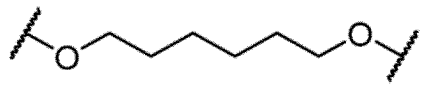

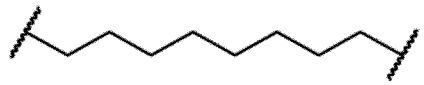

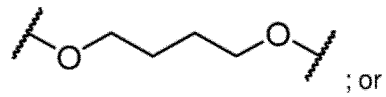 ; or

Signed and Sealed this
Nineteenth Day of November, 2024

Katherine Kelly Vidal
*Director of the United States Patent and Trademark Office*